(12) United States Patent
Hawkes et al.

(10) Patent No.: US 11,488,372 B2
(45) Date of Patent: Nov. 1, 2022

(54) METHOD OF CREATING VIRTUAL PERSONALITY RENDERINGS

(71) Applicants: Matthew Hawkes, South Jordan, UT (US); Mai Nguyen, Salt Lake City, UT (US)

(72) Inventors: Matthew Hawkes, South Jordan, UT (US); Mai Nguyen, Salt Lake City, UT (US)

(*) Notice: Subject to any disclaimer, the term of this patent is extended or adjusted under 35 U.S.C. 154(b) by 0 days.

(21) Appl. No.: 17/131,250

(22) Filed: Dec. 22, 2020

(65) Prior Publication Data

US 2022/0198770 A1 Jun. 23, 2022

(51) Int. Cl.
| | |
|---|---|
| *G06T 19/20* | (2011.01) |
| *G06F 16/901* | (2019.01) |
| *A61B 5/16* | (2006.01) |
| *G06T 15/08* | (2011.01) |

(52) U.S. Cl.
CPC .............. *G06T 19/20* (2013.01); *A61B 5/165* (2013.01); *A61B 5/167* (2013.01); *G06F 16/9027* (2019.01); *G06T 15/08* (2013.01); *G06T 2219/2021* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,768,486 B1* | 7/2004 | Szabo | ..................... | G06T 17/20 345/420 |
| 8,237,714 B1* | 8/2012 | Burke | ..................... | G09B 5/06 345/440 |
| 2004/0217983 A1* | 11/2004 | Forsse | .................. | G06T 11/206 715/700 |
| 2013/0018837 A1* | 1/2013 | Lee | ........................ | A61B 5/165 706/52 |
| 2015/0208976 A1* | 7/2015 | Al-Hashash | ............. | G09B 5/00 434/236 |
| 2016/0292644 A1* | 10/2016 | Drakoulis | ................ | G09B 5/02 |
| 2017/0221374 A1* | 8/2017 | van der Steur | .......... | G09B 7/06 |
| 2017/0242879 A1* | 8/2017 | Hatami-Hanza | ....... | G06N 5/022 |
| 2017/0286862 A1* | 10/2017 | Mourabit | ............... | G06N 3/004 |
| 2018/0121414 A1* | 5/2018 | Nanavati | ............ | G06F 16/3344 |
| 2021/0012097 A1* | 1/2021 | Velthuis | .................. | G06T 19/20 |
| 2021/0374863 A1* | 12/2021 | Zarlengo | ............ | G06F 3/04847 |

\* cited by examiner

*Primary Examiner* — Andrew G Yang
(74) *Attorney, Agent, or Firm* — Steven Rinehart

(57) ABSTRACT

A method and system for creating virtual personality renderings generated from a personality profile exclusively associated with an individual, the rendering depicted in the form of a geometric object in virtual 3D space representing personality traits of the individual. The rendering may comprise a virtual shape having a surface area divided into multiple regions, with each region representative of a personality trait. Personality datapoints may be introduced into the base personality model to generate a unique rendering which is unique for the individual's personality. As personality datapoints are added to personality profile, multiple vectors may project from the base model, causing the base personality model to reconfigure into a non-uniform shape, which is representative of the individual's unique personality. The vectors may represent the magnitude of personality traits.

13 Claims, 16 Drawing Sheets

METHOD OF CREATING VIRTUAL PERSONALITY RENDERINGS

BACKGROUND

Field of the Invention

This invention relates to a method and system for predictive application of virtual personality renderings and more particularly relates to a method of creating a geometric model representative of a personality profile of an individual; and comparative reference of the personality profile with other personality profiles to predict aptitudes, personality patterns, skill sets, and compatibilities, including buying preferences, employment potential, criminal proclivities, and dating matches.

Description of the Related Art

Trait psychology, or dispositional theory, rests on the idea that different people differ from one another on many basic trait dimensions that persist over time and across varying situations. Trait psychology is still in its infancy, and quite often seeks to label individuals with binary traits or characteristics such as extroverted or introverted, intelligent or dumb, nice or mean, hardworking or lazy. Only a very basic level does emerging trait theory start to recognize that, in some respects, individuals are better rated not in binary terms, but across a spectrum, or continuum, with respect to these traits. Trait psychology views personality traits in a largely static manner, and has not yet recognized that personality traits may be dynamic functions of changing environments, stimuli, genetics, and conditioning—much less identified a means of measuring dynamic personality traits and making practical use of those measurements. In general, a person's personality traits, such as generosity and reliability, reflect characteristic patterns of thoughts, intelligence, feelings, and behaviors which are outgrowths of environmental conditioning and genetics.

There have been some attempts in the art analyze personality traits by a merchant, psychologist, or researchers to predict basic preferences or traits. For instance, Amazon® has algorithms in place with attempt to predict which product an individual may be interested in purchasing in the future from past purchases. Psychologist have crude methods of attempting to predict whether criminals will recidivate from past criminal convictions, surveys and conditioning. Even credit reporting agencies attempt to quantify, using credit scores, the likelihood a consumer will pay back future loans based on past actions.

It is increasingly common for third-party aggregators to resell aggregated purchasing, credit, criminal history, income and demographic information to merchants wanting to use the information for commercial purposes, including product marketing.

Proposals for predicting behavior traits of an individual for potential consumerism or in a research project are not yet well-developed. One problem with these behavior tools is that they information gathered with respect to only one personality trait, which is often binary in nature, without any information on how one personality trait influences another.

Even though the above cited systems for predicting behavior traits meet some of the needs of the market, a holistic system for predictive application of virtual personality data; and subsequently use of that personality data in comparison, prediction, ranking and qualification is unknown in the art. It is an object of the present invention to cure these deficiencies as further described below.

SUMMARY

From the foregoing discussion, it should be apparent that a need exists for a method and system for creating virtual personality profiles. The method and system taught below are configured to generate a personality model for an individual that is depicted in the form of a geometric object representing the personality profile for the individual.

A method of creating a virtual personality rendering exclusively associated with a single individual is provided, the steps of the method comprising: manipulating a base shape in virtual three-dimensional (3D) space to create a 3D model of the individual's personality; dividing a surface of the base shape into a plurality of surface regions, each surface region indicative of a personality trait of the individual; subdividing each surface region into a plurality of vectors emanating from the surface region and plotted in the virtual 3D space, each vector indicative of a first datapoint in computer-readable memory exclusively associated with the individual; extending a surface of the base shape outwardly along a vector to an extent indicated by a first datapoint exclusively associated with the vector, the extent defining a terminal end of the first datapoint; and forming a 3D surface intersecting each terminal end of each first data point such that the 3D surface encompasses all plotted first datapoints.

The base shape may comprise a virtual singularity. The singularity may comprise a default set of null first datapoints.

The one of more of the personality traits may comprise extraversion, conscientiousness, risk aversion, novelty seeking, sexuality, humility, intelligence, education, perfectionism, alexithymia, and disinhibition.

In some embodiments, the method may further comprise creating one or more dynamic secondary base shapes in 3D at a terminal end of a first datapoint from which secondary vectors emanate, each secondary vector indicative of a secondary datapoint in computer-readable memory exclusively associated with the individual and the first datapoint.

The method may further comprise creating one or more dynamic secondary regions in 3D at a terminal end of a first data point from which secondary vectors emanate, each secondary vector indicative of a secondary datapoint in computer-readable memory exclusively associated with the individual.

In some embodiments, the method further comprises correlating one first datapoint with a second first datapoint, and adjusting an extent of a terminal end of the one first datapoint to correlate to the terminal end of the second first datapoint.

The method may further comprise correlating a first region with a second region and adjusting a surface of the second region to have correlation with first datapoints in the first region.

The method, in some embodiments, further comprises a step of normalizing each datapoint such that the datapoint represents a plurality of metrics collectively indicated in percentile form, the datapoint exclusively associated with the individual, the datapoint indicating a relative metric to other individuals between 0% and 100%.

The rendering may be formed from a personality profile consisting of a tree data structure, wherein the regions are exclusively associated with nodes within the tree data structure, wherein the datapoints are children of nodes within the tree data structure.

One objective of the disclosure is to provide a virtual personality model that depicts unique personality traits for an individual.

Another objective is to change the shape and dimensions of the base personality model with vectors that represent the magnitude of the personality traits, such that the vectors provide a quick, visual indication of the personality traits for the individual.

Yet another objective is to convert the virtual personality model into a virtual rendering of personality profiles that can be stored in a data storage unit, accessed with a personal communication device, and requested by a merchant in regard to consumers.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

Like reference numerals refer to like parts throughout the various views of the drawings. Reference numerals having a common numeric prefix but ending with a letter indicate multiple instances of the same part.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Figure 1:
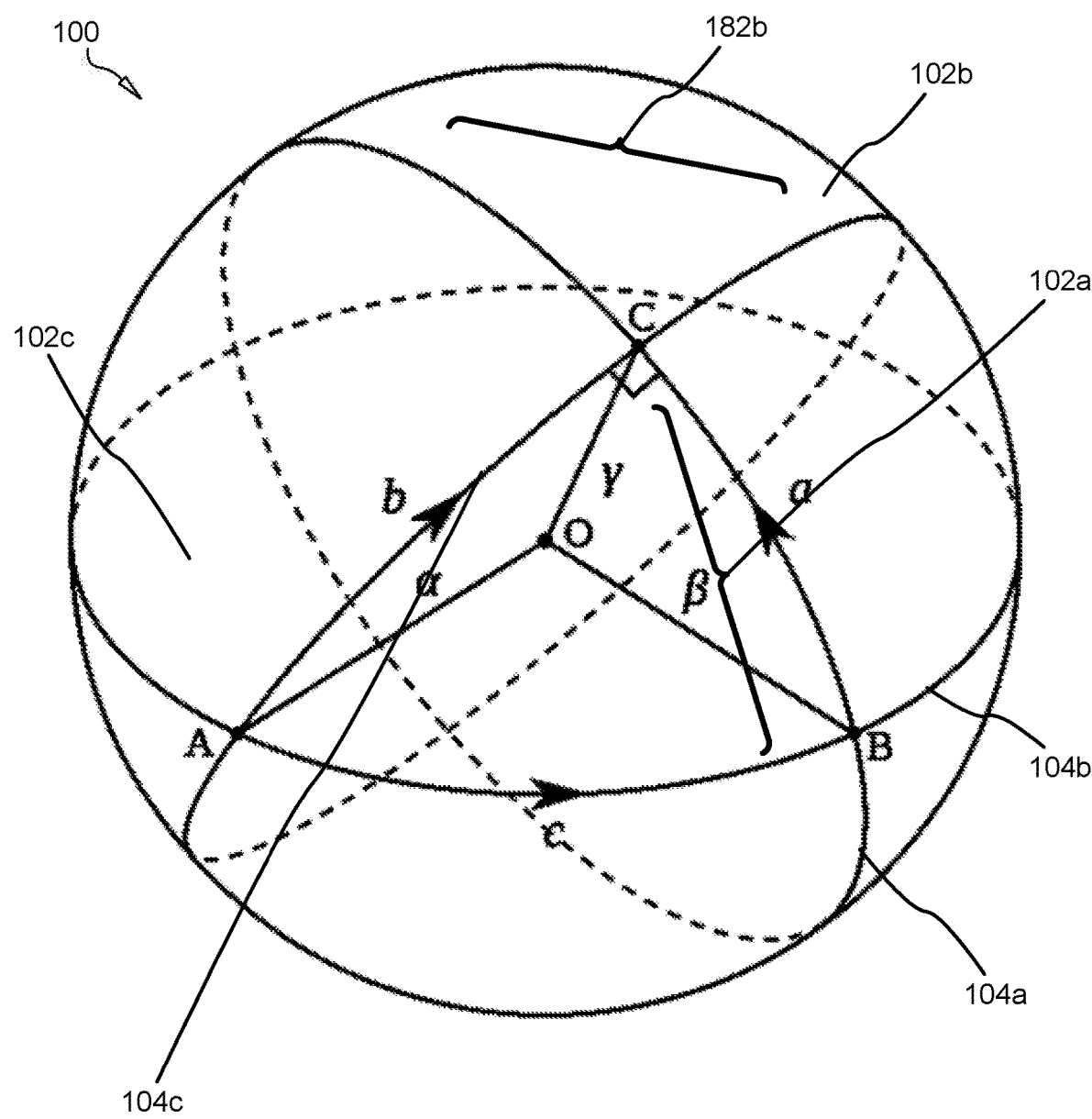
FIG. 1 is a perspective view illustrating an exemplary three-dimensional base personality model, in accordance with the present invention.

FIG. 1 is a perspective view illustrating an exemplary three-dimensional base personality model 100, in accordance with the present invention. A system for predictive application of virtual personality renderings is used to create the base model 100 (or base rendering 100). A system serves to generate a personality model for an individual that is depicted in the form of a geometric object representing the personality profile for the individual. In one possible embodiment, the system provides a base personality model 100 defining a uniform sphere having a surface 105 segregated into multiple regions 102a-c, with each region 102a-c defining a unique personality trait. To generate the base personality model 100, personality data points 104a-c are collected from the individual. Each personality data point represents a magnitude to which the individual exhibits the personality trait on the base personality model 100. The personality datapoints 104a-c are introduced into the base personality model 100 to generate a unique personality model 500 that is unique for the individual's personality.

As personality datapoints 104a-c are added to the personality profile 1700 and the base personality model 100, multiple vectors are projected from the surface 105, causing the base personality model 100 to reconfigure into a non-uniform, shape and dimension, representative of the individual's unique personality. The vectors represent the magnitude of art the personality traits (or datapoints forming a personality trait), and a personality model is rendered which is unique personality to the individual.

In this manner, a system of creating virtual personality rendering reconfigures a default shape (which may be a uniform sphere or singularity either null datapoints or depicting generic personality traits), to a unique personality model, often rendered within virtual 3D space, which graphically and geometrically represents the personality profile 1700 for the individual.

The unique personality model (indicated by way of example below at 900) incorporates sufficient personality datapoints 104 (stored within a personality profile 1700 in some embodiments) that it provides useful representative information on the individual to the individual and third-parties seeking to predict the individuals aptitude, weakness and suitability for future assignments, duties, responsibilities or undertakings. An algorithm (or method or system) generates a rendering 900 from the personality profile and/or the datapoints 104 by modifying the base rendering 100. The personality profile may be computer-readable file in RDBMS which includes the datapoints 104. The personality profile may be dynamic, and be in a constant state of update. In one exemplary embodiment, the personality profile can be instructive to a merchant or a researcher who is analyzing consumer buying preferences, aptitude for a certain employment position, criminal proclivities, dating matches, skills, and general human behavior studies. Further, multiple personality profiles from different individuals can be compared to learn characteristics and predict future personality patterns about the individuals.

Looking again at FIG. 1, the virtual depiction of an individual's personality traits, and magnitude or propensity to possess certain personality traits, is referenced as a base personality model 100. The base personality model 100 may be graphical representation of the generic personality traits common to all individuals. In one possible embodiment, the base personality model 100 is a geometric sphere made up of multiple personality data points. In one embodiment, a small, uniform sphere (or singularity) is the default shape of the base personality model 100. However, in other embodiments, the base personality model 100 is defined by a three-dimensional virtual sphere. In yet other embodiments, the base personality model 100 is defined by a two-dimensional or four-dimensional geometric shape, which may be rotated or exploded by an individual viewing the rendering 900 on a display.

As FIG. 1 illustrates, the base personality model 100 is defined by a surface 105 having multiple, unique regions 102. Each region 102 defines a unique personality trait. Thus, each region 102 on the surface 105 of the base personality model 100 represents a different aspect of that individual's 502 personality. In one exemplary embodiment, region 102a represent a writing ability of the individual's personality. Region 102b may represent a sexual preference personality aspect. Region 102c may represent entertainment preferences and/or an amount of desensitivity to graphic scenes in entertainment. Other regions 102 may represent other aspects of the individual's personality, such as aggressiveness, violent propensities, purchasing habits, interests, hobbies, extent of friendships and willingness to invest therein, or character values ascribed to certain aspects of life and/or personality, such as art, work, interpersonal relationships, music, and the like.

The regions 102 are initially generated on the base personality model 100 when personality data points 104 are collected from the individual. The collected data builds the regions 102 of the base personality model 100. For example, the sphere shown in FIG. 1 is the default shape. Each region 102a-c of the sphere 100 grows when datapoints 104 specific to that person (or individual) are gathered or otherwise determined or estimated.

The region 102 is defined by points A, B and C, in which the length of line B is the radius of sphere 100 from height Y above the center point O of the rendering 100 (and point O is the center point). Each of the regions 102 may comprise spherical caps or hemispheres, in which the volume is Y of a region 102a may be set apart to define a set of personality characteristics, or a personality trait. The volume of region 102a may be defined at $\frac{1}{6}(\pi)(Y)(3\beta^2+Y^2)$. The volume of each region 102 of the rendering 100 representing a personality characteristic may recorded in inches cubed, centimeters cubed, liters, or any 1:4 other standard unit of measurement and stored as an int or float in computer-readable memory, including an RDBMS. In some embodiments, the system rendering the base model 100 is configured to appropriate only certain areas of space on the surface 105 to certain personality traits, thus each personality trait fills a non-uniform area of the surface 105. In some embodiments, regions 102 may overlap. Datapoints 104 within overlapped areas of the regions may be averaged or otherwise combined. The overlap may represent the degree to which one region 102 correlates with another.

Likewise, the surface area of the surface of the region 102a may also be stored in inches squared or centimeters squared in computer-readable memory (in which surface area may be defined as $2\pi\beta Y$ or $\pi(\beta^2+Y^2)$).

Where the region 102a is formed from irregularly-shaped polygons as further described below, appropriate volume and area functions are run on each region using algorithms known to those of skill in the art in some embodiments. The surface area 105 may divided into sub-surface areas 182 covering each region.

Figure 2:
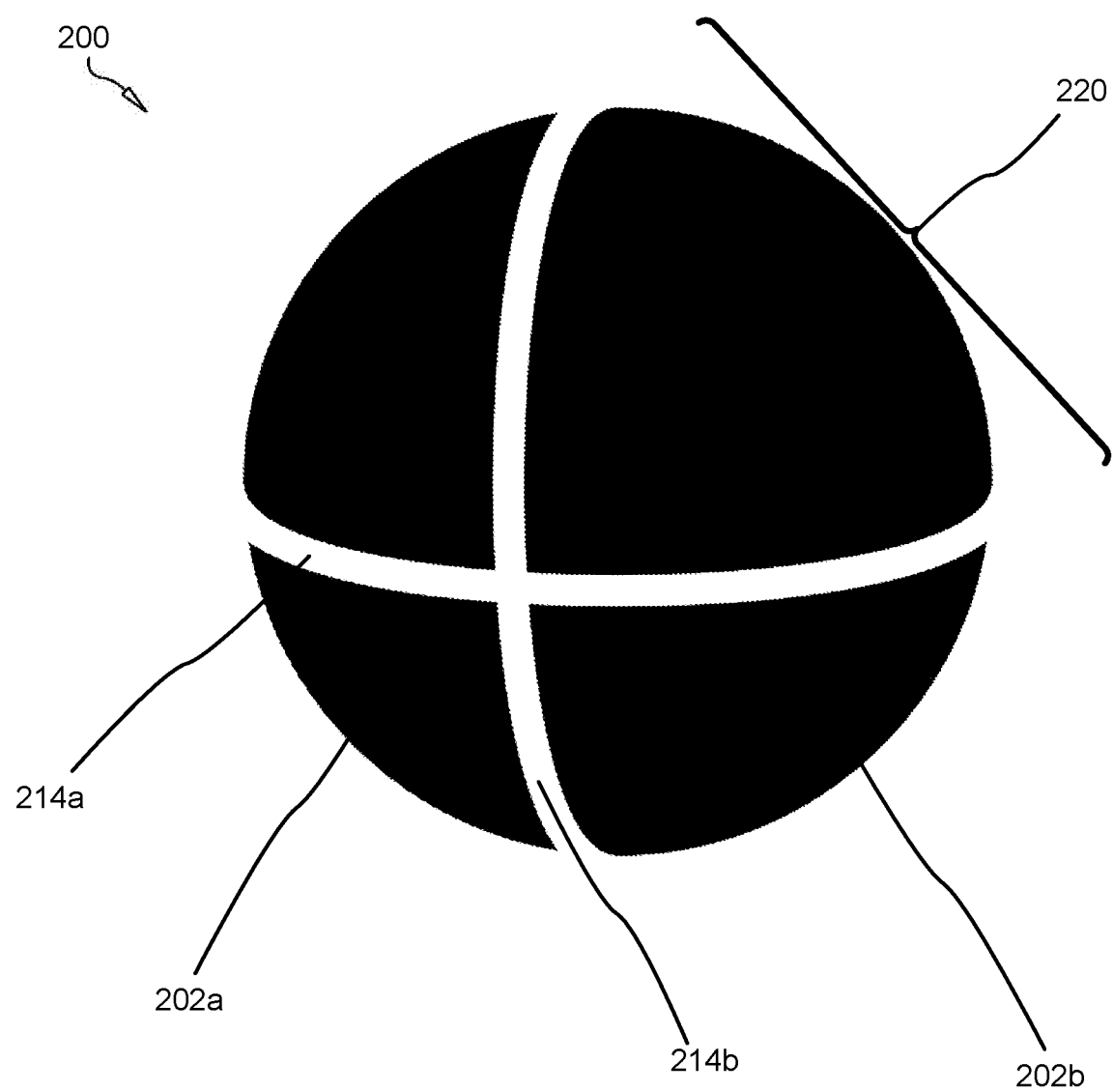
FIG. 2 is a perspective view illustrating an exemplary base personality model having uniform regions, in accordance with the present invention.

FIG. 2 is a perspective view illustrating an exemplary base personality model 200 having uniform regions 202 (which are regions 102 which are uniform in area) in accordance with the present invention. FIG. 2 references an alternative embodiment of a base personality model 200, in which different regions 202a, 202b are represented as a uniform quadrant. Areas in which regions 102 intersect and overlap are represented as quadrant lines 214. However, on other embodiments, the regions 202 can have dissimilar sizes and shapes, depending on the personality trait. For example, some personality traits are given more weight (and more surface area) than others. In some embodiments, the surface area afforded one region 202a in a first individual's rendering may differ from the surface area afforded the same region 202a in a second individual's personality rendering. This exemplary situation could be used when studying criminals and their behavior, for example, when one aspect of a criminal's behavior grows to overtake the majority of the criminal's personality. Thus, the surface area of each region 202 may be dynamic in some embodiments as datapoints 104 are collected for an individual.

Figure 3:
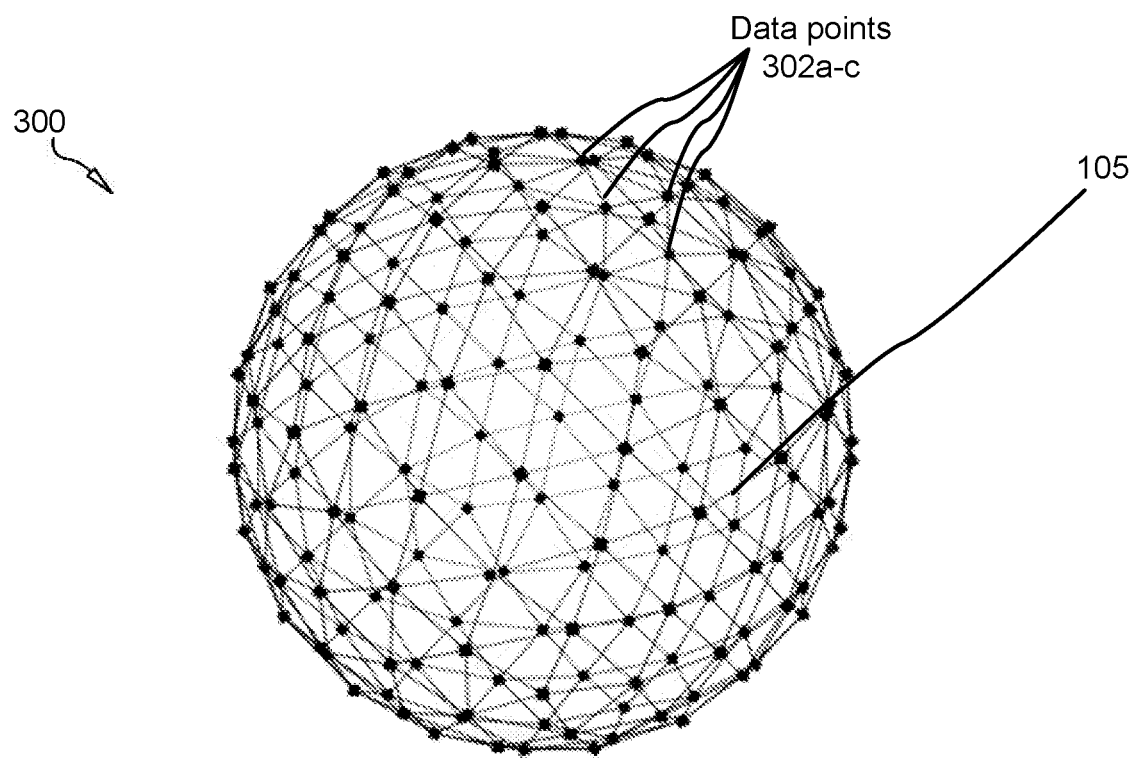
FIG. 3 is a perspective view illustrating an exemplary base personality model having multiple personality datapoints forming a surface in accordance with the present invention.

In another alternative embodiment, shown in FIG. 3, a base personality model 300 is segmented, not into regions 102, but rather the vectors defined by personality datapoints 302a-c are distributed uniformly, or non-uniformly, across the surface 105. As illustrated, each datapoint 302a, 302b, 302c represents a magnitude, or degree (or extent), to which the individual exhibits the personality trait represented by that personality datapoint 302.

The default rendering of a user (or individual 502) with no datapoints 302 may be a singularity 904, or may be a sphere 200. The singularity 904 is manipulated in its virtual 3D appearance to indicate datapoints 302.

Figure 4A:
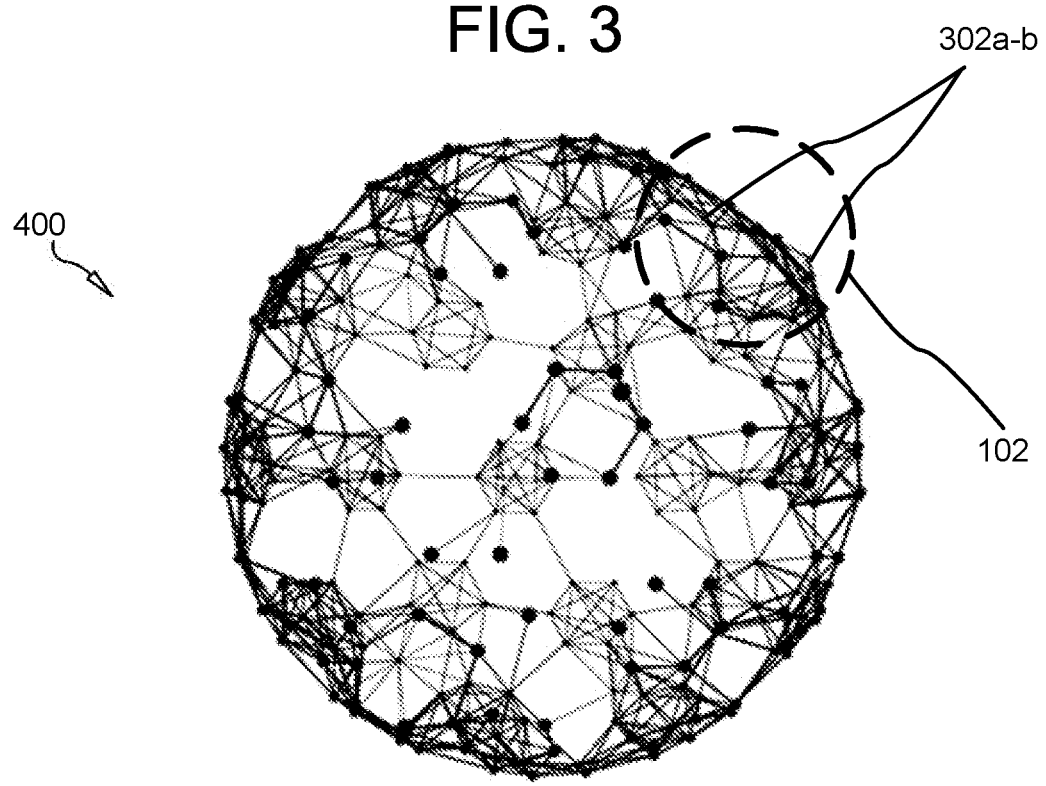
FIG. 4A is a perspective view illustrating an exemplary personality model having multiple regions joined in clusters in accordance with the present invention.
Figure 4B:
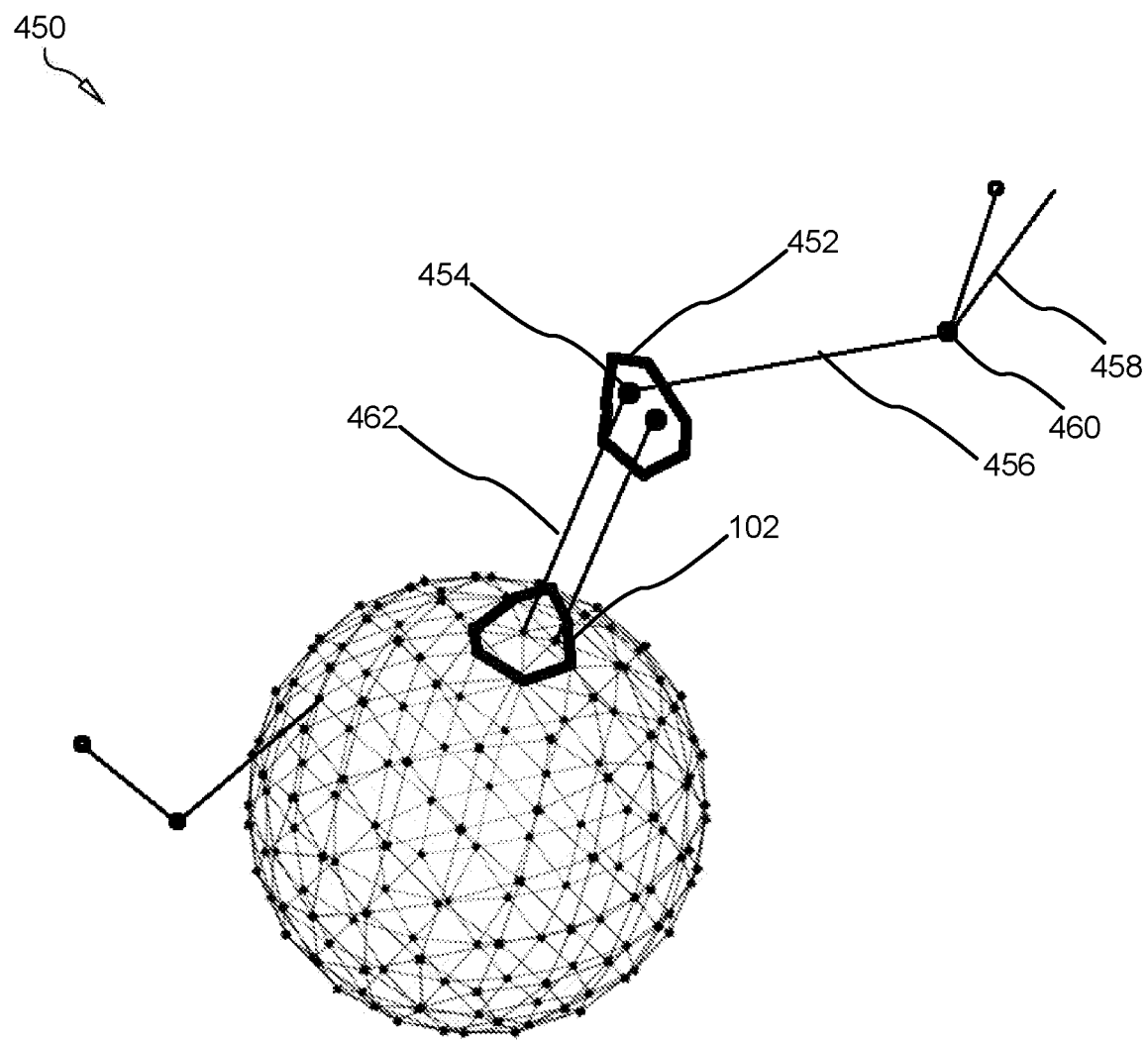
FIG. 4B is a perspective view illustrating an exemplary personality rendering having multiple first and secondary regions in accordance with the present invention.

In yet another embodiment, shown in FIGS. 4A-4B, a personality model 400, 450 is made up of multiple personality data points 302, representative vectors of which can be grouped together in clusters (i.e., regions) 102. The clustered personality data points 302a-b interactively affect each other. For instance, violent propensities may be correlated with a person's athleticism, thus. Thus, the vector representing violence may cause an increase or decrease in athleticism, and these datapoints 302 may be grouped together in region 102. When one personality datapoint in the region 102 is expanded (or lengthened in extent), the others in that same region 102 are expanded also in some embodiments by an order of magnitude manually set by an operator or predetermined by a system. In some embodiments, groups/regions 102 are correlated, and like regions 102 are organized together around the surface of a base personality model 100.

Figure 11:
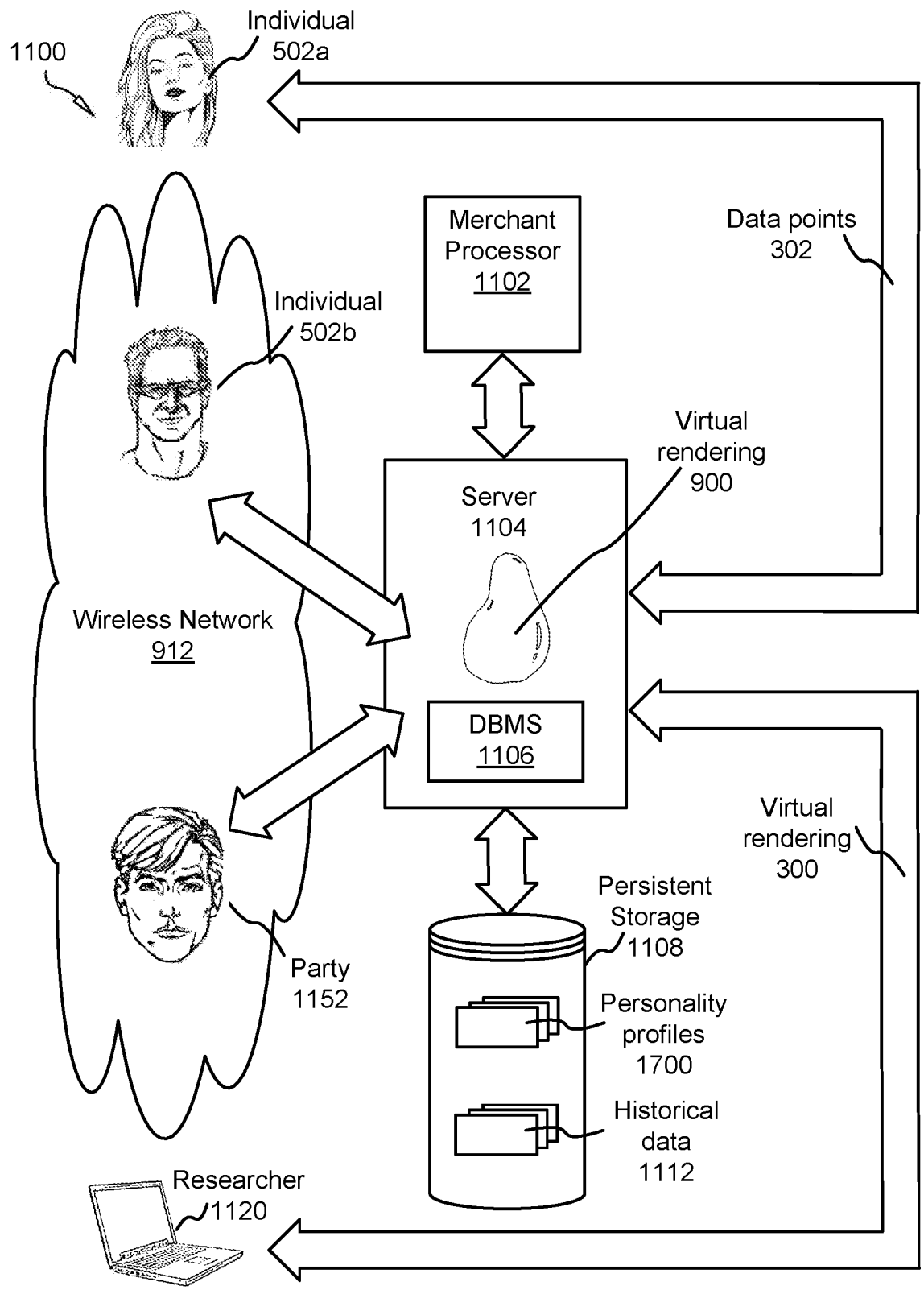
FIG. 11 is a data-entity diagram of an exemplary system for production and predictive application of virtual personality renderings, in accordance with the present invention.

Looking ahead to FIG. 11, a system 1100 provides a collection module 1302 that is configured to collect multiple personality data points 104a-c from the individual. The collection module 1302 can include data collection means that interactively engage with the individual to collect the personality trait datapoints 104, 302. In one embodiment of the collection module 1302, when an individual registers with a system application or website, wow the individual takes a survey (further depicted and described below in relation to FIG. 13) which is designed to elicit personality datapoints from the individual for forming the shape of a region 102. The individual 502 is prompted to answer questions about who they are and what their preferences in life. Other exemplary survey questions may include what the individual sees in a photograph, and a series of binary yes or no questions. Exemplary questions may include:

| | |
|---|---|
| How would I describe myself? | What brought me joy as a child? |
| What brings me joy now? | What's my biggest accomplishment? |
| What's my biggest dream? | What's my biggest fear? |

By answering such questions, personal datapoints 104, 302 are generated. Each collected personality datapoint represents a magnitude, or intensity, graphed onto a vector of the datapoint 104 within a rendering 900. The magnitude of the collected personality datapoints 104, 302 is defined in graphic form as a vector, with each personality datapoint 104, 302 having an exclusively-associated vector with a shape and size indicated in the rendering 450. The vectors are graphical depictions of the magnitude, or intensity, of the datapoints 104, 302 forming personality traits. The greater the individual exhibits a personality trait; the higher the magnitude will be of at least one datapoint 104, 302 within the region 102 representative of that personality trait. And the greater the individual exhibits a personality trait, the longer and wider the vector and region may be. For example, an individual may have a greater fondness for participating in artistic activities, than participating in sporting activities. The vector and region 102 representative of artistic personality proclivity would come to encompass greater surface area than the vector representing a personality for sports or athleticism.

Once collected by the collection subsystem or system 1100, the personality datapoints 104, 302 are populated into the base personality model 100 using a population module 1308. Each collected personality datapoint 104, 302 is populated into a corresponding personality trait region on the surface 1-5 of the base personality model 100, 200, 300. The population of the base personality model 100 can be an automated population.

The vectors representing personality datapoints 104, 302 are magnitudes of the personality traits in the regions 102 of the base personality model 100. The datapoints 104, 302 may be normalized to represent the percentile in which the individual has the personality trait relative to other individuals. The personality datapoints 102, 302 work to reconfigure the more generic base personality model 100, 200, 300 into a unique personality model 900 that represents the entire personality traits for the individual. This reconfiguration generates a more unique personality model 900 for the individual.

Thus, populating the regions 102 of the base personality model 100 with the personality data points 104a-c generates a unique personality model/rendering.

The surface of the regions 102 may be defined by the terminal points 454 on a plurality of vectors emanating from a center point 904 (or O). These terminal points 454 may represent the magnitude (or extent) of data points 103, 302 in computer-readable memory, such as the degree to which the individual represented by the rendering 450 is sexual on a spectrum (or continuum) which may, or may not, have predetermined outer bounds, such as 0 to 10, or which continuum may be normalized to represent the percentile in which the individual falls relative to other individuals for whom data points exist (for instance between 0% and 100%).

Secondary regions 452 may be defined by one or more terminal points 454 (or along midpoints of the vectors 462 or datapoints 104). Secondary vectors 456 may start at terminal points 454 or on the surface of secondary regions 452. Entire default shapes may form at the terminal ends (or midpoints) of vectors 462 representing datapoints 104. Tertiary vectors 458 may also form from terminal ends 460 of secondary vectors 456, and so on.

Figure 5:
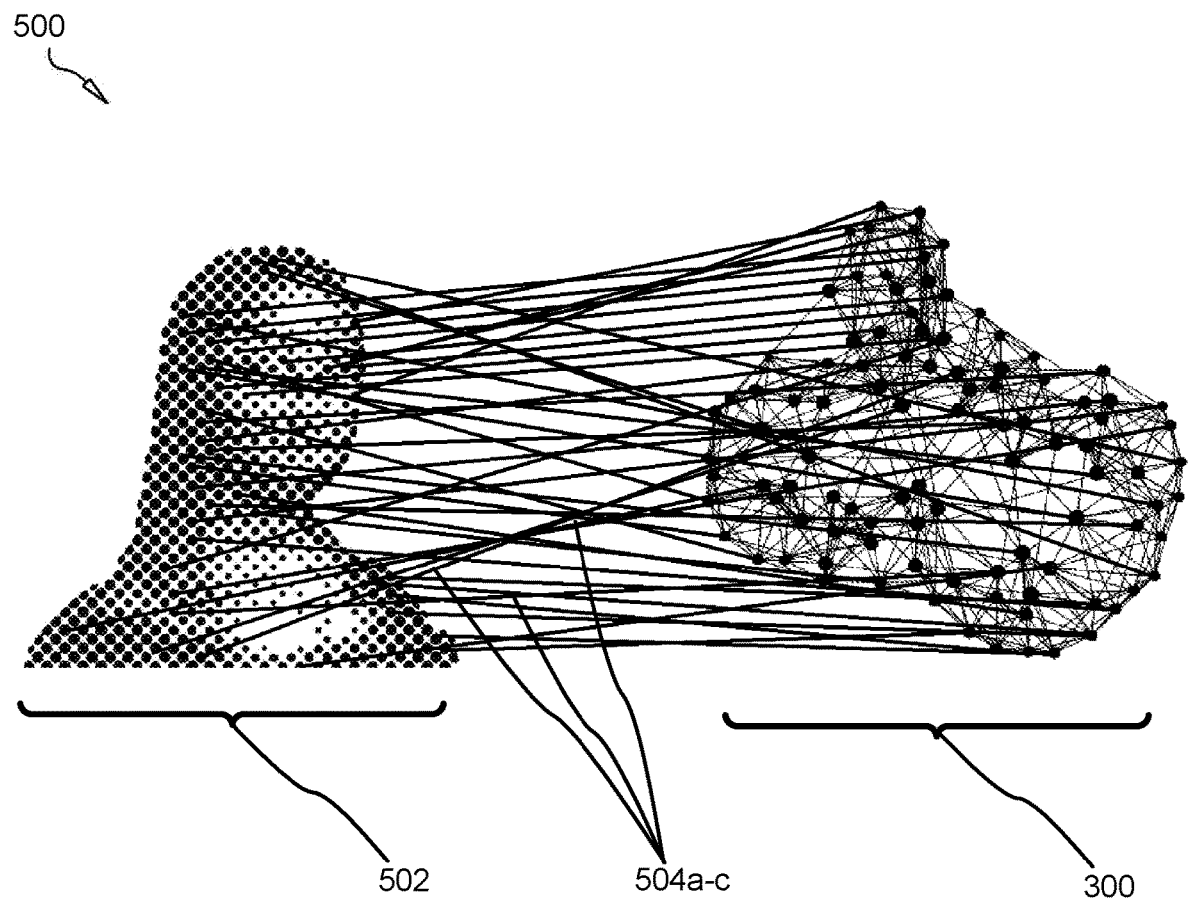
FIG. 5 is a perspective view illustrating an exemplary unique personality model correlated with an illustration of an individual in accordance with the present invention.

FIG. 5 is a perspective view illustrating an exemplary unique personality model 500 correlated with an illustration of an individual in accordance with the present invention. As illustrated, the unique personality model 500 does not exhibit the uniform spherical shape of the base personality model. Rather, the unique personality model 500 has multiple vectors 504a-d projecting therefrom. The vectors 504a-d are representative of a magnitude, or extent, of measured or estimated personality traits. Thus, as personality data points 104a-c are introduced into the base personality model 100, the uniform spherical shape of the base personality model 100 is reconfigured into an irregular-shaped unique personality model 500 defined by multiple vectors 504a-d of varying shape and dimension projecting therefrom. These vectors are associated with the personality of the individual 502.

Figure 6:
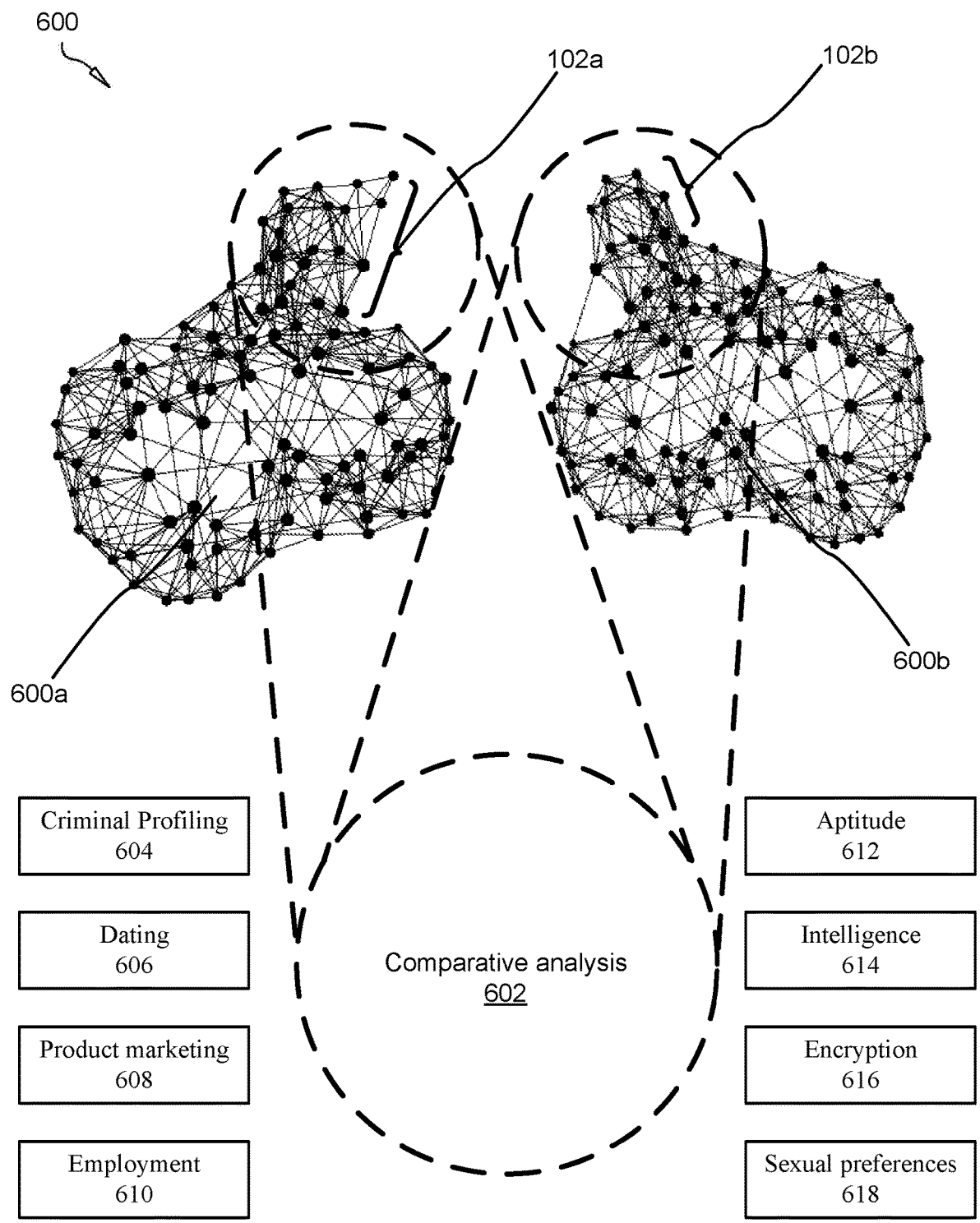
FIG. 6 is a diagram exemplifying a comparative analysis algorithm configured to compare personality traits between the virtual renderings of the individuals, in accordance with the present invention using two exemplary unique personality models in three-dimensions with identical regions highlighted.

FIG. 6 is a diagram exemplifying a comparative analysis algorithm configured to compare personality traits between the virtual renderings of the individuals, in accordance with the present invention using two exemplary unique personality models in three-dimensions with identical regions highlighted.

As discussed previously, the region 102a (defined in FIG. 1 by points A, B and C, in which the length of line B is the radius of sphere from height Y above the center point O of the rendering 100 (and point O is the center point)) may denote a personality trait, such as extraversion. The comparison of the region 102a from rendering 600a against region 102b from rendering 600b may be accomplished, in part, through a comparison of the measured volume of each region 102a, 102b (in which the volume is Y of a region 102a may be set apart to define a set of personality characteristics). The volume of region 102a may be defined as $\frac{1}{6}(\pi)(Y)(3\beta^2+Y^2)$. The comparison may also be realized in part through a comparison of surface area of the regions 102a, 102b (in which surface area may be defined as $2\pi\beta Y$ or $\pi(\beta^2+Y^2)$).

In various embodiments, the volume and surface area of irregularly-shaped regions 102a, 102b of the renderings 600a, 600b may be estimated using Reimann sums or the trapezoidal method, using function, $\int f(x)dx$, where 0 is the default height of a region 102a on sphere 904 (or vector) and a is the longest distance every measured in a rendering 300, with the lower bound of $\int$ being 0 and the upper bound being a.

Figure 7:
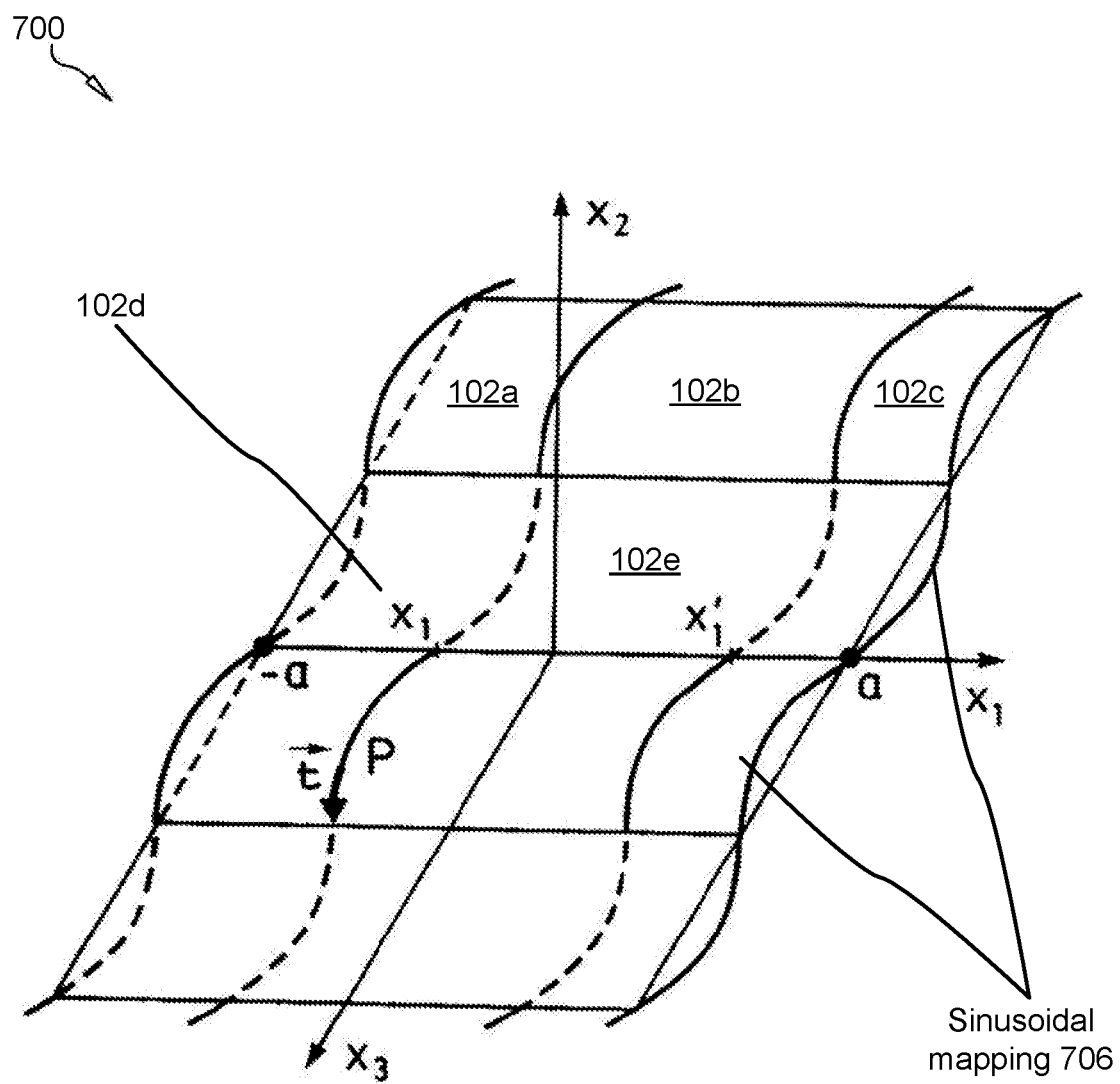
FIG. 7 illustrates an exemplary sinusoidal map used to generate a unique personality model in accordance with the present invention.

For example, FIG. 7 is a perspective view of an exemplary sinusoidal map 700 used to generate the unique personality model. The personality data points 102 are initially plotted on a two-dimensional graph 700. The sinusoidal graphing technique utilizes a two-dimensional graph that is morphed around the sphere-shape of the base personality model 100. This serves to generate the unique personality model 900 of the individual by in applying the map 700 to the base model 100, 200. The unique personality model 900 may then be converted to a personality profile for storage in computer-readable memory and access in a browser such as that depicted at 1000.

In addition to converting the unique personality model to a personality profile 700, the system 1100 is also adapted to convert the unique personality model, or the personality profile 700, into a virtual rendering of the individual. The virtual rendering provides yet another graphical depiction of the personality traits exhibited by the individual. In some embodiments, the virtual rendering may include, without limitation, a two-dimensional image, a three-dimensional image, a four-dimensional image, a video, and clusters of data points arranged around a sphere object.

Figure 8:
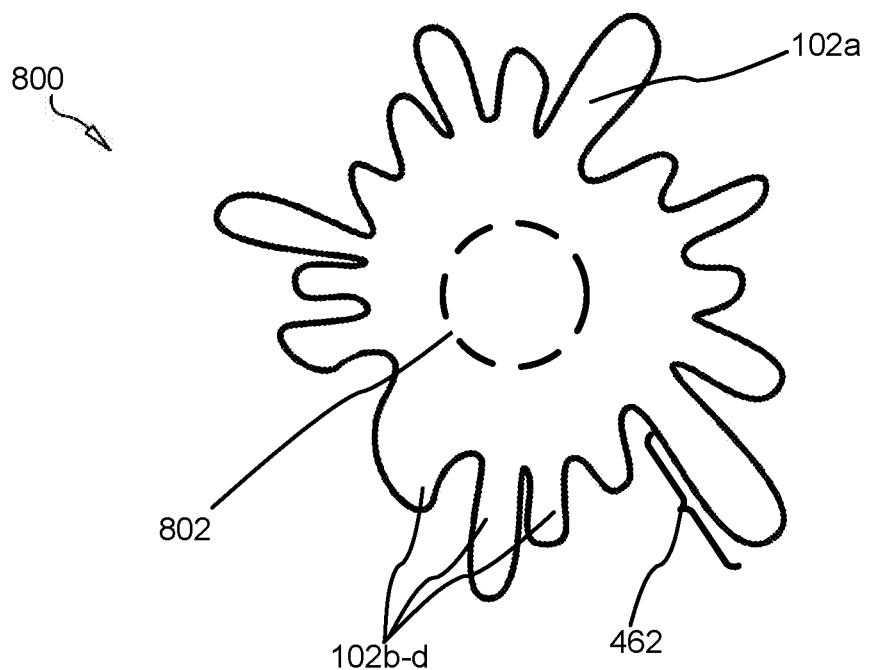
FIG. 8 is a screen shot of an exemplary personality profile in two dimensions in accordance with the present invention.

FIG. 8 shows a screen shot of an exemplary personality profile 800 in two dimensions; whereby the vectors project along an X-axis and a Y-axis in this configuration. However, the unique personality model can also be three-dimensional. In the three-dimensional configuration, the vectors project along an X-axis, a Y-axis, and a Z-axis. However, in other alternative embodiments, the unique personality model 800 may be four-dimensional, or a video.

As graphically depicted in FIG. 8 the vectors 462, which are representations of the magnitude for the collected personality traits, project from a center region 802 of the unique personality model 800. The length and width of the vectors 462 are dependent on the magnitude (or extent) of the personality trait. For example, vector 462 is wider and longer than a single line. This length is indicative that the personality trait represented by vector 462 has a greater magnitude than the personality trait represented by other vectors. The wide nature of vector 462 relative to other vectors indicates the individual exclusively associated with vector 462 over represents this personality trait.

Through analysis of tens of thousands, hundreds of thousands, or millions of renderings 500, 800, the regions 102 of the rendering 500, 800 may be tied both to sequences in DNA genomes or even to physiological characteristics, for instance modeling may show, or add further support to, the relationships between brain regions and rendering 800 regions 102, such as the following associations.

| | |
|---|---|
| Extraversion 620 | Potentially influenced by size of dorsolateral prefrontal cortex and the amygdala. |
| Risk Aversion 624 | Potentially influenced by size and shape of the insular cortex as well as orbitofrontal, occipital and parietal regions of the brain. |
| Perfectionism 632 | Potentially influenced by size and shape of basal ganglia. |
| Alexithymia 634 | Potentially influenced by size and shape of posterior cingulate cortex and thalamus. |
| Disinhibition 636 | Potentially influenced by BMI. |
| Obsessionality 640 | Potentially influenced by damage to basal ganglia. |

Figure 9:
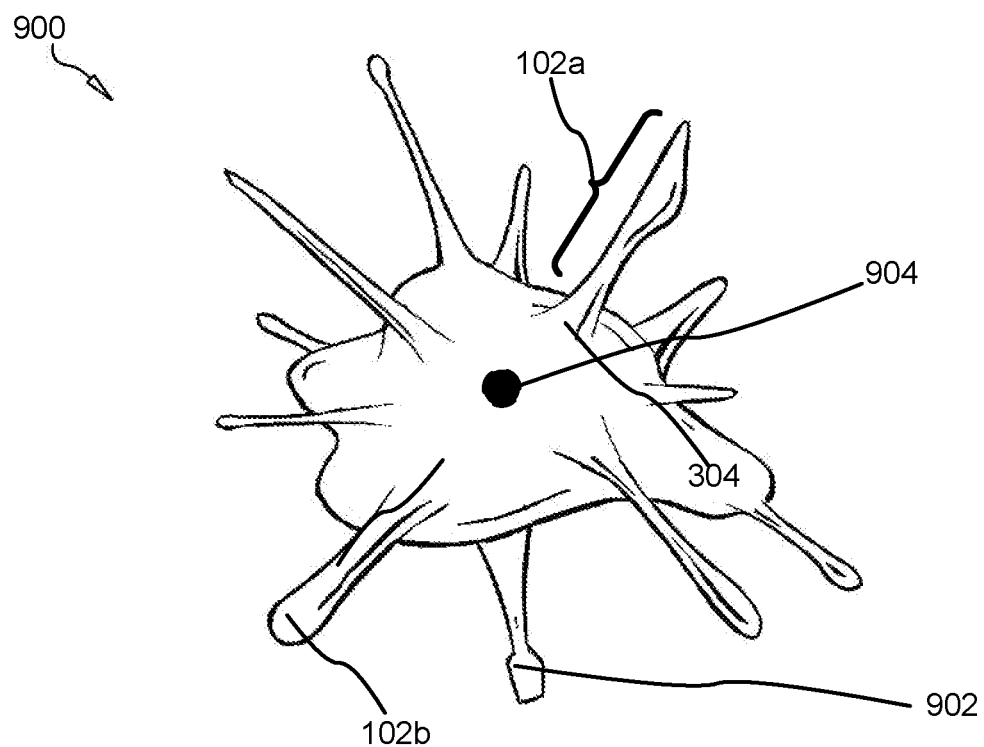
FIG. 9 is a perspective view illustrating a three-dimensional personality model, in accordance with the present invention.

For example, FIG. 9 is a perspective view illustrating a three-dimensional personality model, in accordance with the present invention. FIG. 9 shows a graphical depiction of a unique personality model 900 reconfigured to exhibit three-dimensions. As in the two-dimensional embodiment, the vectors project from a center region 904 of the unique personality model 900 in varying shapes and dimensions, depending on the magnitude of the personality trait. In this illustration, vector 902 is wider and longer at its terminal end than other vectors, showing that the personality trait depicted by vector 902 as having a larger magnitude.

The vectors are graphical depictions of the personality data points, projecting from the center region 904 of the unique personality model 900, increasing in distance from the center region 904 with the degree to which the individual exhibits the personality trait. In all cases of unique personality models, the magnitude of the vector 902 is calculated to H generate the appropriate dimension and shape for the represented personality trait. For example, each vector can receive a score which is relative to a baseline for a personality trait. The vectors projects in shapes and dimensions, relative to each other. However, predetermined values of shape and dimension for the vectors may also be provided to determine the graphical depiction thereof.

Examples of personality traits which may be represented by regions 102 include:

| | |
|---|---|
| Extraversion 620 | Outgoing and projective personality behavior. |
| Conscientiousness 622 | Deference for the welfare of other's in speech and behavior. |
| Risk Aversion 624 | Over deference of consideration for risk in decision-making. |
| Novelty Seeking 626 | Impulsive, excitement-realizing behavior. |
| Self-esteem 628 | Belief in the value of one's self. |
| Humility 630 | Behavior indicative of sincere modesty, desire for praise and meekness. |
| Perfectionism 632 | Obsessive regulation of oneself and actions |
| Alexithymia 634 | Unwillingness to express emotions |
| Disinhibition 636 | Inability to restrain one's actions, impulses and/or thoughts. |
| Obsessionality 640 | Anxiety induced by disturbing thoughts and/or emotions. |

In some embodiments, the vectors 902 do not trace back to the center region 904 of the unique personality model 900; but rather, to the terminal end of another personality data point 102a-c. This embodiment allows secondary vectors to impart a tree-like shape to the overall rendering 900, with secondary vectors 456 emanating from terminal ends 452 of vectors 902. Further, with the clusters of personality data-points 102, the vectors 902 are configured to bulge outwardly at the lateral, after projecting out and away from the surface of the unique personality model 900.

It is significant to note that an individual exhibiting low incidence of a personality trait, below a predetermined threshold, may be exclusively associated with a rendering 900 having an inverted vector 902 which recesses into the surface of the base model 100. Thus, instead of projecting outwardly, the vector 902 may recess back into the unique personality model 900, creating a depression on the surface 105 of the default geometric object 100, 200.

For example, an individual 502 who has a very passive personality may have a recessed vector for the aggressiveness personality trait; and a large projecting vector for the passive personality trait. Thus, the system 1100 may be configured to change the shape and dimensions of the base personality model 100 using vectors representing the magnitude of the personality traits, such that the vectors provide a quick, visual indication of the personality traits for the individual. Regions 102 may also be negative.

Figure 10:
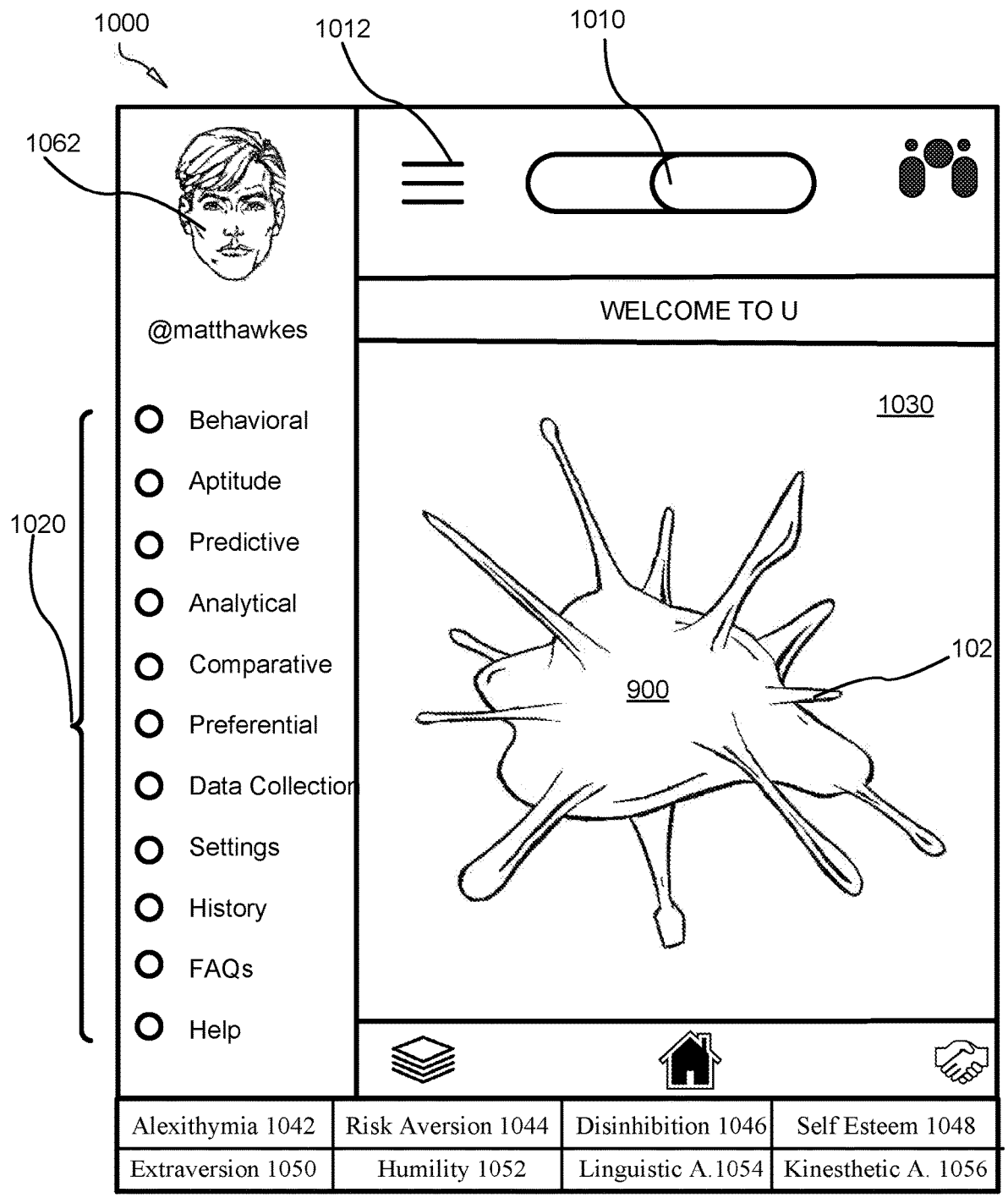
FIG. 10 is an illustrative browser displaying an exemplary interface adapted to facilitate analysis of a virtual rendering exclusively associated with the individual in accordance with the present invention.

FIG. 10 is an illustrative browser displaying an exemplary interface adapted to facilitate analysis of a virtual rendering exclusively associated with the individual in accordance with the present invention.

In various embodiments, the individual 502 for whom the rendering 900 is exclusively associated may view the rendering 900 in virtual 3D space 1030 as shown within a browser or application on a personal computer device or DPD (data processing device). The rendering 900 may be manipulated in virtual 3D space 1030 by the user (who may be the individual 502), including exploding, rotating, zooming in, and zooming out. Within the interface 1000, the personality traits are indicated within virtual buttons 1042-1056. When one of the virtual buttons 1042-1056 is activated by the user, the region 102 within the rendering 900 exclusively associated with the personality trait indicated in the activated virtual button 1042-1056 is highlighted within the rendering 900. Thus, the user may select the region of the rendering 900 which the user would like to analyze. The personality traits may include one or more of: alexithymia, risk aversion, disinhibition, self esteem, extraversion, humility or different types of intelligence, including logical-mathematical intelligence, spatial intelligence, linguistic intelligence, interpersonal intelligence, and naturalistic intelligence.

In various embodiments, the user may select the purpose from the left menu bar 1020 for which the user is analyzing the rendering 900. The user may compare the rendering 900 to renderings of other individuals using the navigation bar 1020. The user may be analyzing the rendering 900 to ascertain the aptitude of the individual 502 for a specific purpose, in which case the aptitude virtual control is selected. Activation of the aptitude virtual control may result in the rendering 900 changing to display only regions 102 associated with aptitude. In various embodiments, the rendering also changes when behavior is selected to show regions only associated with behaviors. Likewise the same is true for preferences, including entertainment preferences, sexual preferences, religious preferences, and environmental preferences. When the data collection control is selected, the interface 1000 may switch to a survey mode such as that shown in FIG. 16 below.

For example, FIG. 9 shows a relationship that illustrates the generation of a virtual rendering 900 of an individual 902. The virtual rendering 900 is generated from personality data points 302a-c that are internal to the individual 902. The personality data points 302a-c are referenced from the unique personality model. The virtual rendering 900 may simply be a different graphical reference than the spherical-shaped or vector-populated personality models discussed above. In any case, the personality models, the personality profiles, and the virtual rendering are all based on the personality data points collected by the collection module 1302.

FIG. 10 references the comparison between two different virtual renderings 1002a, 1002b. A comparative analysis algorithm 1000 is configured to compare personality traits 1004a, 1004b between the virtual renderings 1002a, 1002b of the individuals. Specifically, the comparative analysis algorithm 1000 analyzes the personality data points and generates comparison data that assesses the differences and similarities in the two virtual renderings 1002a, 1002b. However, other comparison techniques may include, without limitation, mapping databases that are populated with individual data points, machine learning, artificial intelligence, surveys, and other comparative analysis techniques known in the art.

In the example shown in FIG. 10, a group of personality data points 102a-b generate vectors that project from the surface of each sphere. The personality data points are compared to analyze how similar two individuals are in regard to their personalities. Examples of predictive and comparative research personality data points which can be compared may include, without limitation, criminal profiling, dating matching, aptitude for certain tasks or employment, and the like.

In some embodiments, the personality models, the personality profiles, and the virtual rendering, and personality data points thereof, may be stored on a data storage unit, such as a remote server or cloud. The personality data points, and images may be accessed through a personal communication device by the individual, or an interested party. In one non-limiting embodiment, the system 1100 may monetize access to the data storage unit by charging a fee to the merchant or researcher.

The interface 1000 displays a facial image 1062 of the individual 502 in order to provide reference. The name and contact information for the individual 502 may also display next to the facial image 1062. The interface 1000 may also display menus to select from at least one of the following: personality traits, data collections, graphical representations of the unique personality model, settings, and a FAQ page. The navigation bar 1020 may provide for other selections, such as logging on or off the system application.

Turning now to FIG. 11, a data entity diagram 1100 illustrates the steps necessary for an individual 502 or interested party 1152 to view the personality data points in a desired rendering 800, 900. Once viewed in this manner, the personality of the individual 502 can be analyzed for marketing and/or research purposes and/or other purposes. In one embodiment, a first individual 502a engages with the collection module 1302 on a server 1104 to answer survey questions, and thereby provides personality datapoints 104. The personality datapoints 104, 302 are collected and transmitted to a data storage unit 1108, such as persistent storage within a remote server 1104. In one non-limiting embodiment, a database management system 1106 (DBMS) is provides to define, manipulate, retrieve, and manage the personality data points 104a in the data storage unit 1104.

Additionally, the personality data points 104 can be stored in a database, such as a persistent storage 1108, in case there is a power shortage. The persistent storage 1108 may include magnetic media, such as hard disk drives and tape and various forms of optical media such as DVD. The personality data points 104 can be segregated into personality profiles 1700, and historical data 1112 of the individual 502.

As shown in the data entity diagram 1100, a unique personality model 800, 900 is generated using the collected personality data points 104 of the first individual 502a. As discussed above, the vectors and regions 102 define personality traits, and bounds thereof relative to other individuals. The system 1100 allows interested parties 1152, such as merchants or researchers, to access the unique personality model 900 for marketing and research purposes. In one embodiment, a merchant 1152 may utilize a merchant processor 1102 to access and view the generated unique personality model 900. The merchant 1152 may utilize this information to predict personality patterns, and thereby market to the first individual 502.

In another possible use of the unique personality model 1700, a researcher 1152 can access the data storage unit 1104 to compare personality data points 104 for two individuals 502a, 502b. As discussed above the comparative analysis can be useful for comparing the different personality traits for individuals 1046-1052. This comparative analysis is useful for studying criminal behavior or personalities in a specific demographic, for example. Further, the researcher 1152 can input data and notes into the data storage unit 1104 or persistent storage 1108 for future research, which may or may not be publicly-accessible or which information may also comprise datapoints 104 incorporated into the personality profile 1700.

Figure 12:
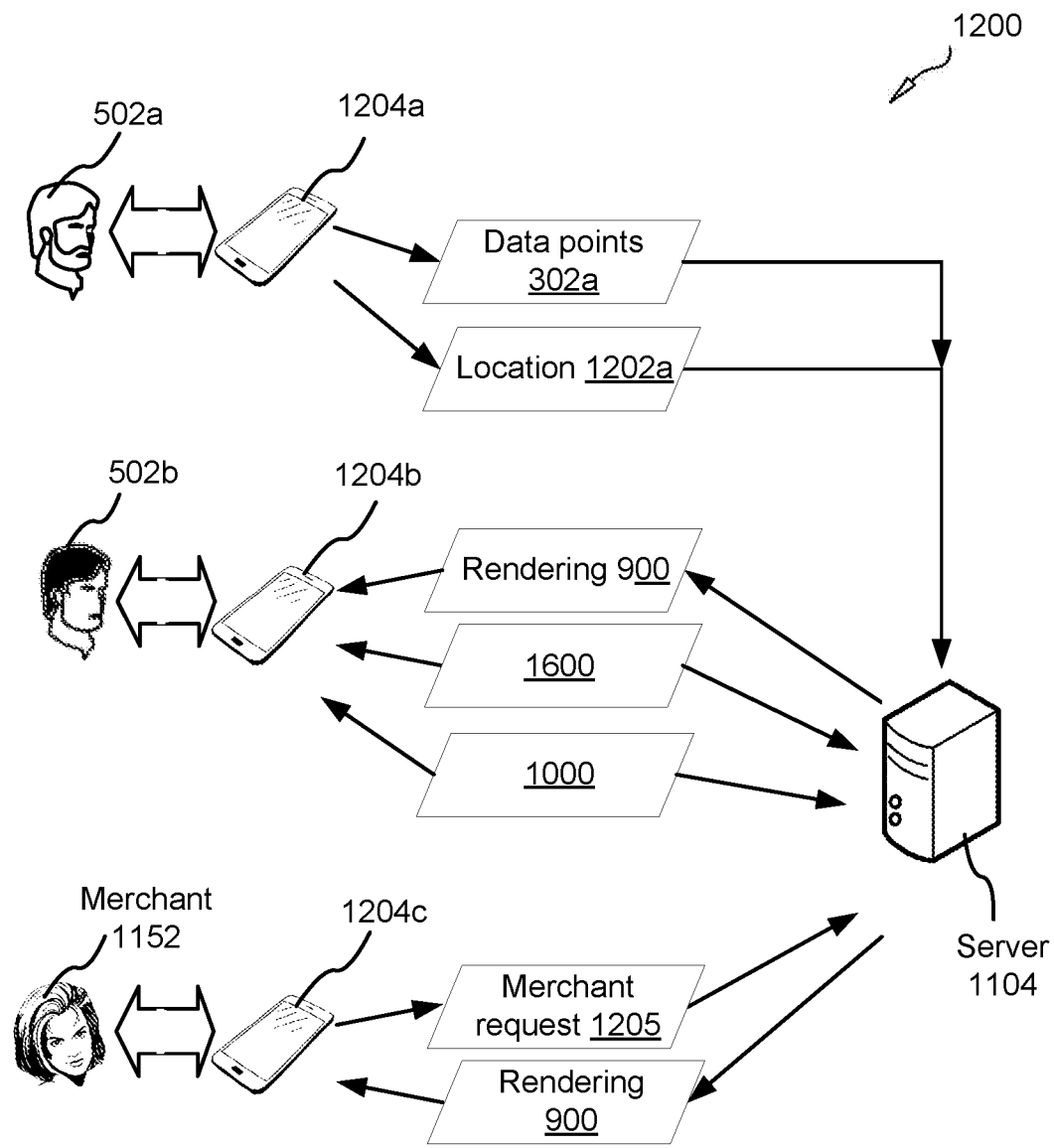
FIG. 12 is a data-entity diagram of an exemplary merchant access subsystem, in accordance with the present invention.

Turning now to FIG. 12, a block diagram for a merchant access subsystem 1200 illustrates the elements that assist a merchant 1152 in accessing and utilizing the unique personality model 900 of an individual 502a. From this information, a merchant 1152 may perform various marketing efforts to contact or sell to consumers. The marketing efforts are based on the different personality traits for individual 502a.

As illustrated, a first consumer or merchant 1152 utilizes a communication device 1204c to access and download a rendering 900 comprising personality datapoints 104 from a data storage unit 1104. The communication device 1204a under the control of the individual 502 also provides the location 1202a of the individual 502. This can be performed through a GPS, Google Maps™, or other location technologies known in the art. This location 1202a feature is combined with the personality data points 302a for subsequent consumption by the merchant 1152 in the form of the rendering 900. Thus, the merchant 1152 will know, not only the personality traits and predictive behavior of the individual 502, but also the movements and location of the consumer 502.

A second consumer 502b is also analyzed for personality traits and location by the merchant 1152. The second consumer 502b utilizes a communication device 1202b to access and download the interface 1000 and survey interface 1600. Personality data points 104 are uploaded to the same data storage unit 1104 to which the first consumer 502a uploaded or downloaded personality data points 104. The communication device 1202b also provides the location of the second consumer 502b. The merchant 1152 may utilize the location of the second consumer 502b and the personality data point 104a for marketing efforts. In addition, the second consumer 502b may view a virtual rendering 900 generated by the personality data points 302. From the virtual rendering 900, the second consumer 502b may self-assess personality traits, and aptitudes relative to the individual 502a.

Looking again at FIG. 12, the merchant 1152 also utilizes a communication device 1204c to transmit a merchant request 1205 to the data storage unit 1104. The merchant request 1205 is a request to access and view datapoints 104 in graphic form. Multiple renderings 900 may be relayed to the merchant 1152. In this manner, unique personalities of different individuals 502 can be compared to learn characteristics and predict future personality patterns about the individuals/consumers 502.

Figure 13:
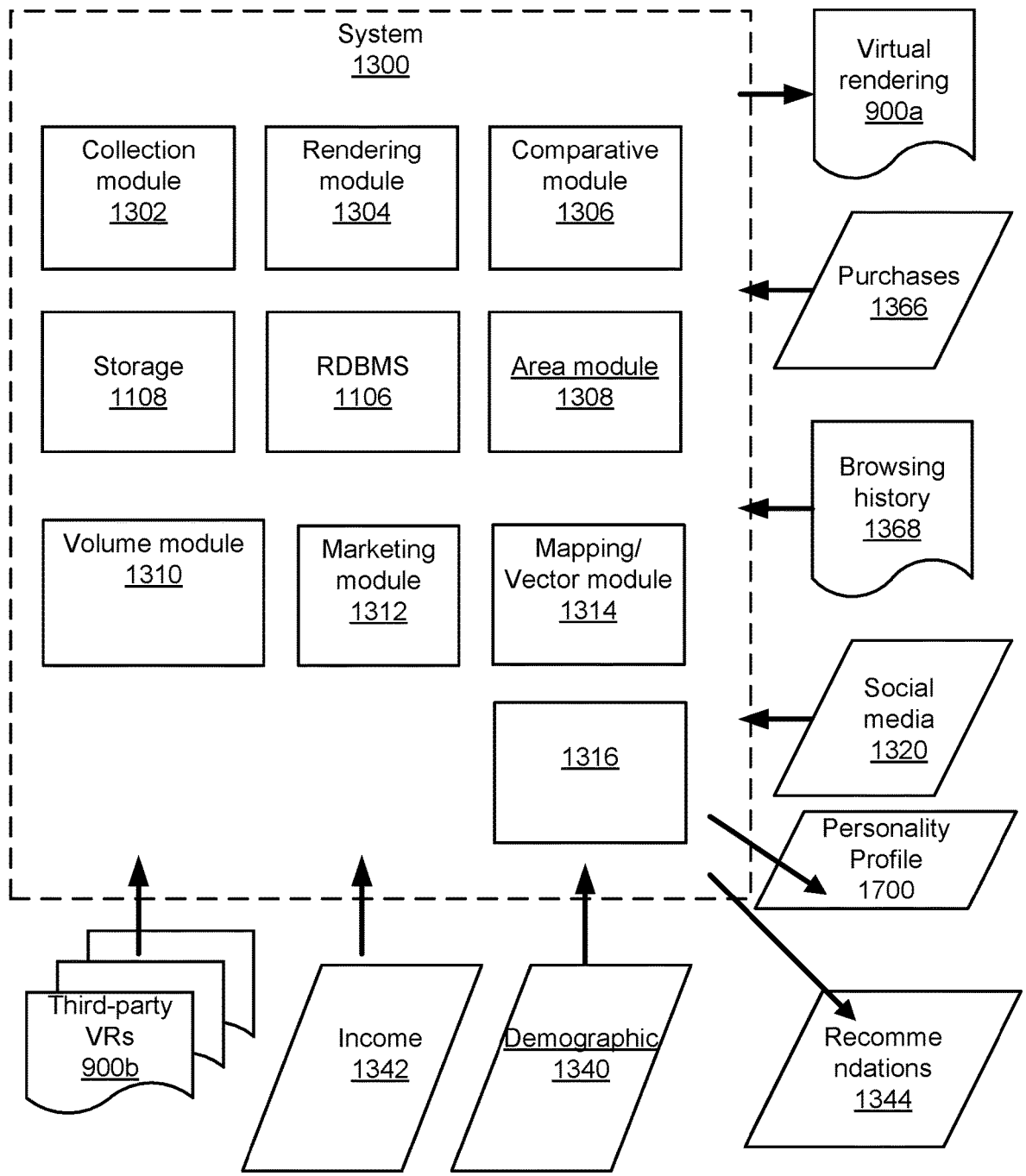
FIG. 13 is a block diagram of a rendering distribution module, in accordance with the present invention.

FIG. 13 shows a block diagram of a rendering distribution module 1300 comprising multiple modules and data points that populate the system 1100 to create the virtual renderings 900. Once created, the virtual renderings 900 can be shared for research purposes. As discussed above, the virtual rendering 900 may simply be a different graphical reference than the spherical-shaped or vector-populated personality models discussed above. And different datapoints 104 may be collected to generate a virtual rendering 900.

As illustrated in the diagram of the rendering distribution system 1300, a collection module 1302 is used to collect the personality datapoints 104 from the individual 502, often suing a survey interface 1600. A rendering module 1304 may be configured to then generate a virtual rendering 900 which provides a graphical representation of the personality datapoints 104. A comparative module 1306 is configured to compare regions 102 of the different virtual renderings 900 from different individuals and/or the overall surface contouring. Such comparative analysis can be useful for comparing the different personality traits for individuals 502a, 502b.

A data storage unit 1104 and a database management system 1106 (DBMS) are used to store, archive, and prepare for retrieval, the personality datapoints 104. In addition, various other modules may be utilized by the rendering distribution system 1300. The system 1300 may be a module in a larger system. This can include an area module 1308 configured to measure the surface area of a region 102, a volume module 1310 configured to measure a volume of a region 102.

A marketing module 1312 may be configured to identifier individuals 502 whose renderings 900 render such individuals 502 susceptible to certain marketing by way of consumer preferences. A vector module 1314 may be configured to draw vectors 462 within the rendering 900 with the vectors 462 representative of normalized datapoints 104, and for comparisons of virtual renderings 900 and personality datapoints 104 of differing individuals 502.

The system 1300 may comprise a mapping module 1314 configured to map a sinusoidal map 700 onto a default shape 100. The system may also comprise an elimination module 1316 configured to eliminate certain regions 102 from the rendering 900, said regions associated with one of preferences, behaviors, race, intelligence, and gender. The elimination module may also be configured to eliminate data from the rendering which can be used to identify the individual exclusively-associated with the rendering by name, race and/or ethnicity, religion, age, and/or gender.

Multiple datapoints 104 populate the rendering distribution module 1300. The datapoints 104 help generate a virtual rendering 900 which can subsequently be utilized for marketing or research purposes, prediction and comparison. In one embodiment, the datapoints 104 include a purchases datapoint 1366 comprising a computer-readable file comprising historical purchases made by the individual 502. The purchases datapoint 1366 can help the rendering distribution system 1300 better understand the personality traits of potential consumers 502. Another datapoint 1368 can include a browsing history datapoint 1368 which indicates personality traits derived from web-viewing preferences. The browsing history data point 1368 can show the impulses and preferences of the potential consumer 502.

Continuing with the data points used by the rendering distribution module 1300, a social media datapoint 1320 can be utilized by the rendering distribution system 1300 to understand the various social media sites that the individual 502 visits and comments. Those skilled in the art will recognize that social media outlets are effective wells of personality information. Furthermore, a demographic datapoint 1340 can be utilized by the rendering distribution system 1300 to understand the demographics of the individual 502, including wealth, race, gender, and height. This can include the habitat location, race, and ethnicity. When combined with the other datapoints 104, the demographic data point 1340 paints a clearer picture of the individual's 502 personality traits.

Yet another datapoint is an income data point 1342, which is useful in determining the spending capacity of the potential consumer. Yet another datapoint 104 is a third-party virtual rendering 900b, in which a third party provides personality datapoints, and renderings thereof, of the individual. This third party may be a credit bureau or court. This can give an outsider perspective to further enhance the personality analysis of the individual 502.

Once all the datapoints 104 are inputted into the rendering distribution system 1300, a processor 1402 analyzes the datapoints 104. Also, the individual modules can assess portions of the datapoints 104. For example, the comparative module 1306 may be used to compare the income data point 1342 with the browsing history data point 1368. This can be useful for assessing the websites visited by a low-income individual and a high-income individual. A recommendation 1344 is provided based on this analysis, in some cases to a merchant 1152.

For example, the rendering distribution system 1300 can recommend that the individual 502 has a personality propensity to purchase items quickly on the first page of a website without clicking links to secondary pages. This quick-trigger personality trait (impulsiveness) may indicate to a merchant 1152 to place the high cost items on the initial landing page of a marketing website. Further, the rendering distribution module/system 1300 may also be configured to populate datapoints 104 within a region 102, a personality profile 1700, and a virtual rendering 900 for the individual. This can provide a graphical depiction of the individual's personality that the merchant can scan amongst many others in a short period of time.

The modules of the system 1300 may output the personality profile 1700 into the RDBMS 1106 and computer-readable memory.

Figure 14:
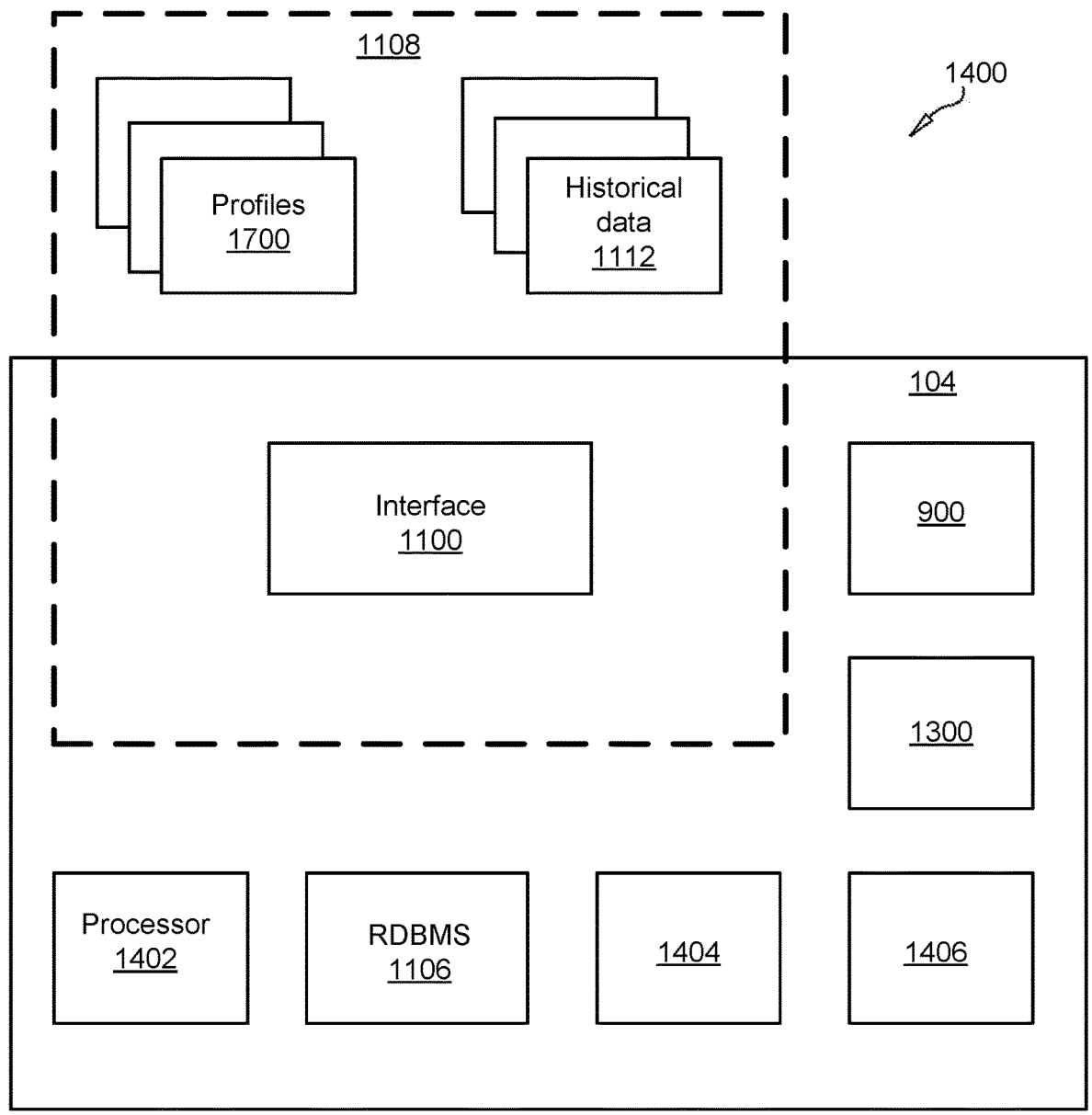
FIG. 14 is a block diagram for a processor system, in accordance with the present invention.

Turning now to FIG. 14, a block diagram for a processor system 1400 that processes and regulates the aforementioned data points, personality model, personality profile 1700, and virtual renderings 800, 900 is referenced. The processor system 1400 comprises a persistent storage 1108 that stores the personality datapoints 104, and then in segregates the datapoints 104 into profiles 1700 and historical data 1112 of the individual 502.

Continuing with the processor system 1400, a data storage unit 1108 for remote storage of the personality datapoints 104 is also provided. The data storage unit 1108 comprises a processor chip 1402, a relational database management system 1106, a first computing subsystem 1404, a second computing subsystem 1406, a system 1300, and an interface 1100 for viewing the personality model 900, a personality profile 1700, and a virtual rendering 900.

Figure 15:
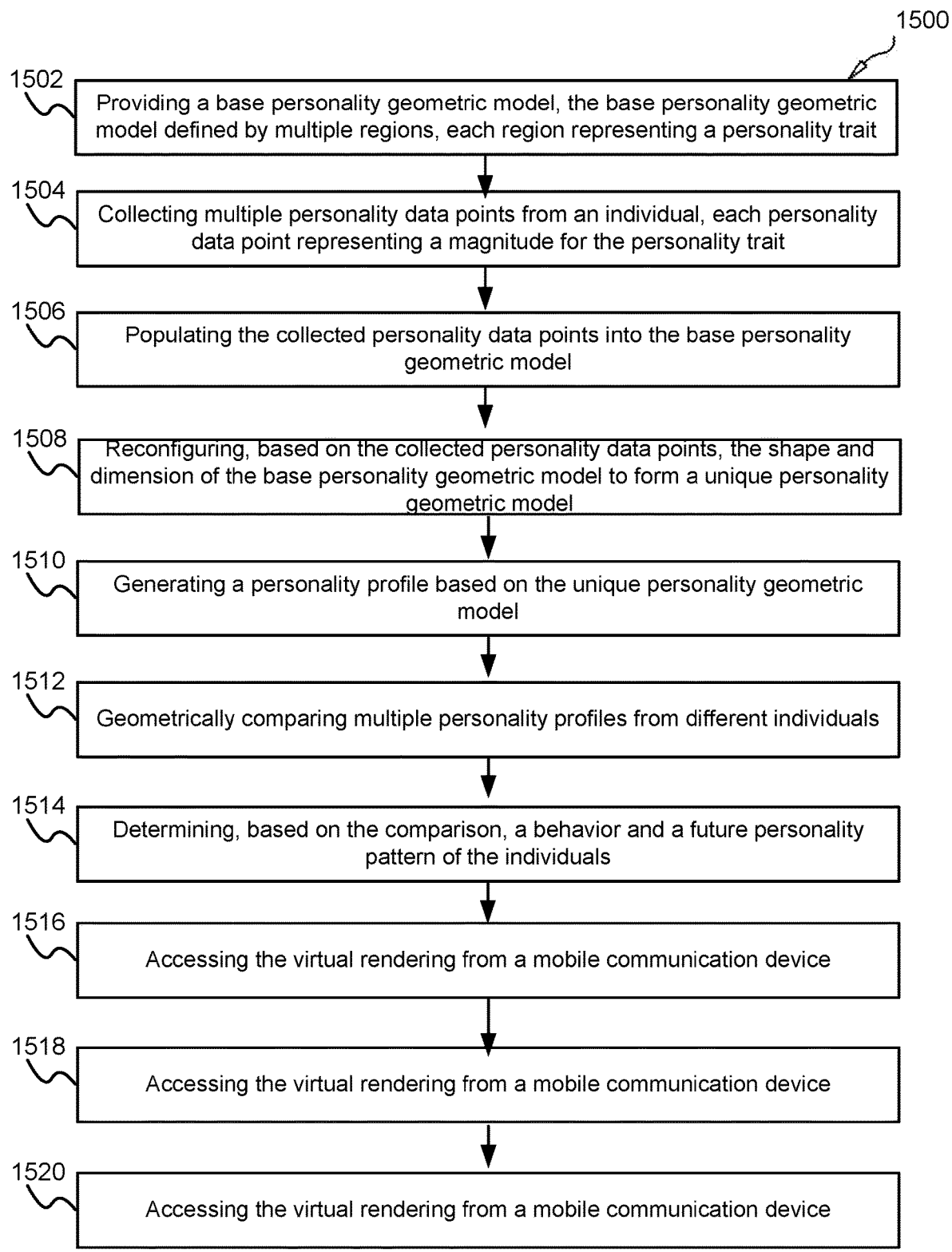
FIG. 15 is a flow chart of a method for predictive application of virtual personality renderings, in accordance with the present invention.

Looking at the flowchart of FIG. 15, a method 1500 method for predictive application of virtual personality renderings is referenced. The method 1500 in the disclosed embodiments substantially includes the steps necessary to carry out the functions presented above with respect to the operation of the described method 1500. In one embodiment, the method 1500 includes an initial Step 1502 of providing a base personality model, the base personality model defined by multiple regions, each region representing a personality trait. In one non-limiting embodiment, the base personality model comprises a rendering 900. In some embodiments, the base personality model may begin with a uniform shape such as a sphere or singularity.

The base shape 100 may comprises regions 102. The regions 102 can represent a myriad of types of personality traits as described above. For example, region 102a may represent a writing ability personality trait. In other embodiments, region 102b represents sexual preferences. In yet another embodiment, region 102c represents entertainment preferences. Other region may represent other aspects of a person's personality, such as aggressiveness (or violent propensities), purchasing habits, interests, hobbies, extent of friendships, or value ascribed by the person to certain aspects of life.

The method 1500 also may include a Step 1504 of collecting multiple personality datapoints 104 from an individual 502, each personality datapoint 104 representing a magnitude, or extent, for the personality trait. The method 1500 may be configured to collect personality datapoints 104 from the individual 502 using a survey or through analysis of historical records related to the individuals' preferences or behavior. Each personality datapoint 104 represents a magnitude to which the individual 502 exhibits the personality trait. The personality datapoints 104 may be added to the base personality model 100. In some embodiments, the step 1504 of collecting multiple personality data points from an individual, includes participating in a survey on an interface 1600, answering questions, and analyzing photographs.

In a further embodiments, the method 1500 includes a Step 1506 of populating the collected personality datapoints 104 into the base personality model 100.

The method 1500 also includes a Step 1508 of reconfiguring, based on the collected personality datapoints 104, the shape and dimension of the base personality model 100 to form a unique personality model/rendering 900. Multiple vectors 462, representing the magnitude of the personality traits, and thereby the datapoints 104, project from the unique personality model 900. As personality datapoints 104 are added, the vectors cause the personality model to reconfigure into a unique shape and dimension, representative of the individual's unique personality.

In some embodiments, a Step 1510 comprises generating a personality profile 1700 based on the unique personality model 900 or vice versa. In one possible embodiment, the personality profile 1700 is displayed as a virtual rendering 900. In some embodiments, the virtual rendering 800 may include, without limitation, a two-dimensional image 800, a three-dimensional image 900, a four-dimensional image, and/or a video which may be time-lapse.

The method 1500 also may include a Step 1512 of comparing multiple personality profiles 1700 from different individuals 502. In another embodiment, Step 1512 of comparing personality profiles 1700 is performed with a sinusoidal map 700 and/or artificial intelligence.

In a further embodiment, the method 1500 includes a Step 1514 of determining, based on the comparison, a behavior and a future personality pattern of the individual 502. The determination is performed by various processors 1402, machine learning algorithms, and comparison analysis.

In another embodiment, the method 1500 further comprises storing the virtual rendering 900 on a data storage unit 1104. In another embodiment, the method 1500 further comprises a Step 1516 of accessing the virtual rendering 900 from a mobile communication device 1204. In another embodiment, the method 1500 further comprises a Step 1518 of requesting, by a merchant, a virtual rendering of at least one consumer. In another embodiment, the method 1500 further comprises a Step 1520 of identifying the location of the consumer. In alternative embodiments of the method, another step can include providing the merchant 1152 with the virtual rendering 900 or a plurality, and the location of the consumer 502.

In conclusion, a method 1500 and system 1100 for predictive application of virtual personality renderings generates a predictive personality model representative of a personality profile 1700 or rendering 900 for an individual 502. The predictive personality model may be defined by a virtual sphere having multiple regions 102, with each region defining a unique personality trait. Multiple personality datapoints 104 are collected from an individual. Each personality datapoint 104 represents a magnitude to which the individual 502 exhibits one or more personality trait. The personality data points are added to the base personality model 100, 200 in some embodiments. Multiple vectors 462, representing the magnitude of the personality traits, project from the unique personality model 900. As personality datapoints 104 are added to the personality profile 1700, the vectors cause the personality model to reconfigure to a unique shape and dimension, representative of the individual's 502 unique personality. The unique predictive personality models from different individuals 502 can be compared to learn characteristics and predict future personality patterns about the individuals.

Figure 16:
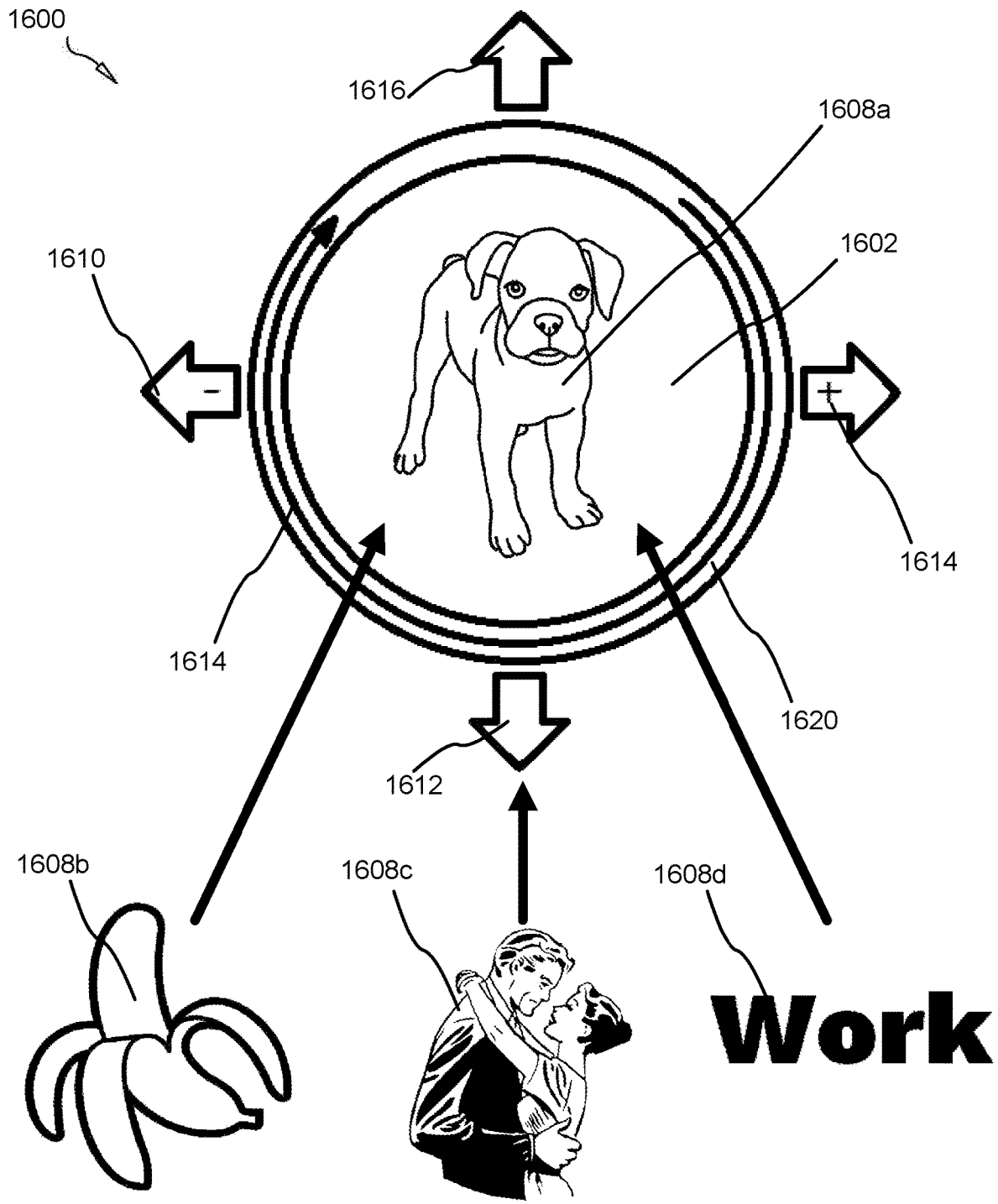
FIG. 16 illustrates a virtual rendering a survey interface adapted to collect preliminary data from a user in accordance with the present invention.

FIG. 16 illustrates a virtual rendering a survey interface 1600 adapted to collect preliminary data from a user.

In various embodiments, a virtual personality rendering 900 is initially created by sampling the individual 900 exclusively associated with the rendering 900 by submitting the user/individual 502 to a survey administered through the virtual survey interface 1600. The virtual survey interface 1600 may be adapted to gather either binary information, such as "like" and "dislike" and/or preference information distributed across a continuum 1614. Thus, responses gathered from the user 502 may be stored in computer-readable memory as Boolean or as an integer representing the strength of a response.

In the shown embodiments, the user is prompted to like or dislike the image 1608a displayed at the center of the virtual rendering 1600. The user may click on, or swipe in the direction of, the virtual button 1614 to indicate a preference, or like, for the image 1608 displayed. These images 1608 may include a type of fruit 1608b, an activity spelled out 1608d within the virtual survey interface 1600 such as "work," or activities depicted in graphic form, such as sexual activities 1608c. A letter following a numeral in indicates components indicates another instance of the component in the embodiment. Reference to a component indicated with a letter following the numeral which reference is made without the following letter indicates any of instance of the component in the embodiment.

In various embodiments, tactile indication in the negative direction (or in the direction of virtual button 1610) indicates dislike of the image 1608, while tactile indication in the positive direction (or in the direction of the virtual button 1614) indicates like, or approval of, the image 1608. Tactile interaction with the virtual survey interface 1600 in the direction of virtual button 1616 may indicate unfamiliarity with the shown image, while tactile activation of the virtual button 1612 may indicate apathy toward the displayed image 1608. In various embodiments, a degree of approval may be indicated by the user through tactile swiping in a position on, or relative to, a spectrum or continuum 1614 which may be indicated by a circle circumscribing the image 1608.

The datapoints 104 gathered from images 1608 shown successively in the virtual survey interface 1600 may be used initially as datapoints 302 in creating a personality profile 1700 which is used in creating the virtual rendering 900, and used to initially populate the regions 102 and rendering 900.

Figure 17:
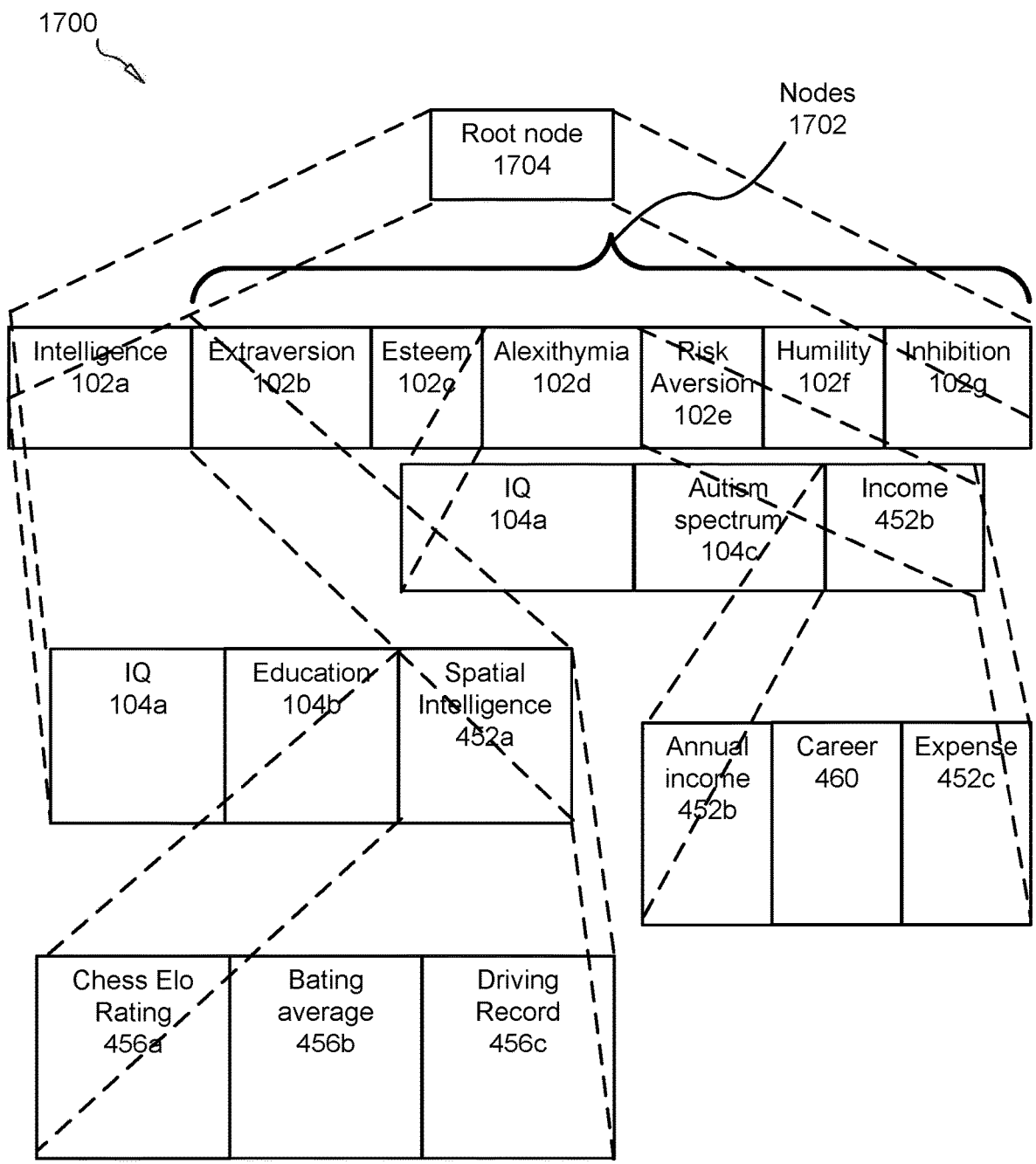
FIG. 17 is a data layout diagram illustrating one embodiment of a personality profile in accordance with the present invention.

FIG. 17 is a data layout diagram illustrating one embodiment of a personality profile 1700 in accordance with the present invention.

In some embodiments, a personality profile 1700 is generated from the datapoints 104 or alternatively from the rendering 900. The personality profile 1700 is unique to the personality of the individual 502. To generate the personality profile 1700, datapoints 104 must be collected. The datapoints 104 are organized into regions 102 both within the rendering 900 and within the personality profile 1700. The personality profile 1700 may comprise a binary tree. It is the unique personality of each individual 502 which is depicted graphically with irregularly-shaped vectors 462 protruding from a default shape 100, 200. That is to say the present method and systems taught herein include converting alphanumeric digits, photographs, charts, graphs, historical information, and other metrics associated with an individual 502 into datapoints 104 and/or vectors 462 within the rendering 900. The personality profile 1700 displayed in a rendering 900 may be more advantageous in graphical form to analysis because of the human ability to analyze patterns and graphical data more easily than numbers. The personality profile 1700 in rendered form 900 also provides metrics that can be compared more easily than matrices and numerals.

The personality profile 1700 may comprise a computer-readable file. In various embodiments, the personality profile 1700 comprises a plurality of nodes representing regions 102 within a tree data structure forming the personality profile 1700 in whole or in part. The personality profile 1700 may comprise a tree data structure comprising a plurality of nodes 1702 representing regions 102, secondary regions 452, tertiary regions, and so on. The nodes 1702 may initially represent regions 102, but additionally or alternatively represent datapoints 104.

The personality profile 1700 for the default shape 100 may comprise an empty set. The root node 1704 may comprise the nodes 1702 as children. In various embodiments, each child node 1702 comprises a plurality of datapoints 104 and consists of only one secondary region 452.

Computationally, the nodes 1702 may bifurcate in a directed or undirected graph. The datapoints 104 may be children of the nodes 1702 or alternatively secondary regions 452, which are also nodes, may be children of the nodes 1702.

In various embodiments, some of the datapoints 104 form part of a plurality of regions 102. For instance, intelligence quotient (IQ) may be a datapoint 104a in both the intelligence region 102a and the alexithymia region 102d. In these embodiments, datapoint 104 may itself be a node with children representative of the regions in which datapoint 104a is included, including the extent to which datapoint 104a affects that region. Datapoint 104a may comprises an integer, float or like indicates an extent to which datapoint 104a aggravate, exaggerates or mitigates other datapoints 104 within any region forming the rendering 900.

The region 102a exclusively associated with intelligence generally may comprise datapoints 104a-456c specifically relating to differing types of intelligence, such as spatial intelligence, IQ, and the like.

The personality profile 1700 is stored in a data storage unit 1108, such as a server 1104 or remote database. The individual 502 and interested parties, i.e., merchant 1152, researcher, can access the personality profile 1700 through use of a communication device.

In some embodiments, multiple personality profiles 1700 of different individuals can be compared to better predict personality patterns. Those skilled in the art will recognize that this comparative information is useful for marketers, or researchers studying personality trends in a group of individuals. In one non-limiting embodiment, the generation of the unique personality model 1700 may be performed with a sinusoidal map 700. The unique personality may then be converted to a rendering 900.

The present invention has been developed in response to the present state of the art, and in particular, in response to the problems and needs in the art that have not yet been fully solved by currently available marketing systems that collect and use consumer personality traits. Accordingly, the present invention has been developed to provide a method and system for predictive application of virtual personality renderings that overcome many or all the above-discussed shortcomings in the art.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of creating a virtual personality rendering exclusively associated with a single individual, the steps of the method comprising:
   manipulating a base shape in virtual three-dimensional (3D) space to create a 3D model of the individual's personality;
   dividing a surface of the base shape into a plurality of surface regions, each surface region indicative of a personality trait of the individual, each region forming an irregularly-shaped polygon covering an area on the base shape which is not congruent with an area on the base shape of any other region;
   subdividing each surface region into a plurality of vectors emanating from the surface region and plotted in the virtual 3D space, each vector indicative of a first datapoint in computer-readable memory exclusively associated with the individual;
   wherein a majority of the regions overlap with two or more adjacent regions to form an overlap;
   wherein datapoints within the overlap are averaged;
   extending a surface of the base shape outwardly along a vector to an extent indicated by a first datapoint exclusively associated with the vector, the extent defining a terminal end of the first datapoint;
   wherein a magnitude of the vector is directly correlated with an intensity of a personality trait exclusively associated with the vector;
   forming a 3D surface intersecting each terminal end of each first data point such that the 3D surface encompasses all plotted first datapoints.

2. The method of claim 1, wherein the base shape comprises a virtual singularity.

3. The method of claim 2, wherein the singularity comprises a default set of null first datapoints.

4. The method of claim 1, wherein one of more of the personality traits comprises extraversion, conscientiousness, risk aversion, novelty seeking, sexuality, humility, intelligence, education, perfectionism, alexithymia, and disinhibition.

5. The method of claim 1, further comprising creating one or more dynamic secondary base shapes in 3D at a terminal end of a first datapoint from which secondary vectors emanate, each secondary vector indicative of a secondary datapoint in computer-readable memory exclusively associated with the individual and the first datapoint.

6. The method of claim 1, further comprising creating one or more dynamic secondary regions in 3D at a terminal end of a first data point from which secondary vectors emanate, each secondary vector indicative of a secondary datapoint in computer-readable memory exclusively associated with the individual.

7. The method of claim 1, further comprising correlating one first datapoint with a second first datapoint, and adjusting an extent of a terminal end of the one first datapoint to correlate to the terminal end of the second first datapoint.

8. The method of claim 1, further comprising correlating a first region with a second region and adjusting a surface of the second region to have correlation with first datapoints in the first region.

9. The method of claim 1, further comprising normalizing each datapoint such that the datapoint represents a plurality of metrics collectively indicated in percentile form, the datapoint exclusively associated with the individual, the datapoint indicating a relative metric to other individuals between 0% and 100%.

10. The method of claim 1, wherein the rendering is formed from a personality profile consisting of a tree data structure, wherein the regions are exclusively associated with nodes within the tree data structure, wherein the datapoints are children of nodes within the tree data structure.

11. The method of claim 1, further comprising adding a plurality of midpoints along one or more vectors.

12. The method of claim 11, further comprising adding a plurality of secondary vectors to each region, each secondary vector emanating from one of a terminal point and a midpoint of a vector, wherein each secondary vector is plotted in the virtual 3D space.

13. The method of claim 12, wherein the vectors and secondary vectors form a tree-like structure above the surface of the base shape.

\* \* \* \* \*